US012279799B2

United States Patent
Harshman et al.

(10) Patent No.: US 12,279,799 B2
(45) Date of Patent: Apr. 22, 2025

(54) SYSTEMS AND METHODS FOR OFF-AXIS TREATMENT OF A VERTEBRAL BODY

(71) Applicant: Stryker Corporation, Kalamazoo, MI (US)

(72) Inventors: Gabriel James Harshman, Portage, MI (US); Christopher Scott Brockman, Kalamazoo, MI (US); Beau Michael Kidman, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/511,157

(22) Filed: Nov. 16, 2023

(65) Prior Publication Data

US 2024/0081883 A1     Mar. 14, 2024

Related U.S. Application Data

(63) Continuation of application No. 17/603,148, filed as application No. PCT/US2020/028989 on Apr. 20, 2020, now Pat. No. 11,849,986.

(Continued)

(51) Int. Cl.
    *A61B 17/88*     (2006.01)
    *A61B 17/16*     (2006.01)
    (Continued)

(52) U.S. Cl.
    CPC ...... *A61B 17/8811* (2013.01); *A61B 17/1642* (2013.01); *A61B 17/3421* (2013.01);
    (Continued)

(58) Field of Classification Search
    CPC ............ A61B 17/8811; A61B 17/8819; A61B 17/8855; A61B 17/1642
    See application file for complete search history.

(56) References Cited

U.S. PATENT DOCUMENTS 3,320,957 A    5/1967   Sokolik
4,326,530 A    4/1982   Fleury, Jr.
(Continued)

FOREIGN PATENT DOCUMENTS

DE      3840466 A1    6/1990
EP      3081252 A1    10/2016
(Continued)

OTHER PUBLICATIONS

English language abstract and machine-assisted English translation for DE 38 40 466 extracted from espacenet.com database on Jan. 8, 2018, 8 pages.

(Continued)

*Primary Examiner* — Anu Ramana
(74) *Attorney, Agent, or Firm* — Howard & Howard Attorneys PLLC

(57) ABSTRACT

Systems and methods for augmenting a vertebral body. An introducer device includes a shaft having a flexible distal portion with a pre-set curve in an unconstrained state. An input provided to an actuator to tension a pulling element to move the pre-set curve to a constrained state in which the distal portion and a flexible sheath conforming to the shaft at least partially straighten. The introducer device is removable from the sheath remaining offset from a longitudinal axis. A spacer hub facilitates proximal movement of the sheath relative to an access cannula expose a balloon through a syringe-style input. A hub of the access cannula may be adjustable to selectively adjust an interference surface relative to a datum. At least two radiopaque markers may be disposed on the sheath with relative positions between the markers viewable on lateral and A-P radiography to determine the location and/or curvature of the sheath.

19 Claims, 21 Drawing Sheets

Related U.S. Application Data

(60) Provisional application No. 62/837,930, filed on Apr. 24, 2019.

(51) Int. Cl.
*A61B 17/34* (2006.01)
*A61B 17/00* (2006.01)
*A61B 17/32* (2006.01)

(52) U.S. Cl.
CPC ...... *A61B 17/3472* (2013.01); *A61B 17/3478* (2013.01); *A61B 17/8819* (2013.01); *A61B 17/8855* (2013.01); *A61B 2017/00261* (2013.01); *A61B 2017/00314* (2013.01); *A61B 2017/00323* (2013.01); *A61B 2017/00331* (2013.01); *A61B 2017/00336* (2013.01); *A61B 2017/320048* (2013.01)

(56) References Cited

U.S. PATENT DOCUMENTS

| | | |
|---|---|---|
| 4,607,626 A | 8/1986 | Borodulin et al. |
| 4,748,969 A | 6/1988 | Wardle |
| 4,947,827 A | 8/1990 | Opie et al. |
| 5,108,404 A | 4/1992 | Scholten et al. |
| 5,209,749 A | 5/1993 | Buelna |
| 5,224,488 A | 7/1993 | Neuffer |
| 5,242,461 A | 9/1993 | Kortenbach et al. |
| 5,282,821 A | 2/1994 | Donahue |
| 5,292,330 A | 3/1994 | Shutt |
| 5,295,980 A | 3/1994 | Ersek |
| 5,306,272 A | 4/1994 | Cohen et al. |
| 5,327,906 A | 7/1994 | Fideler |
| 5,445,639 A | 8/1995 | Kuslich et al. |
| 5,455,365 A | 10/1995 | Winter et al. |
| 5,499,981 A | 3/1996 | Kordis |
| 5,501,654 A | 3/1996 | Failla et al. |
| 5,540,693 A | 7/1996 | Fisher |
| 5,591,170 A | 1/1997 | Spievack et al. |
| 5,624,431 A | 4/1997 | Gerry et al. |
| 5,695,515 A | 12/1997 | Orejola |
| 5,709,697 A | 1/1998 | Ratcliff et al. |
| 5,814,044 A | 9/1998 | Hooven |
| 5,843,103 A | 12/1998 | Wulfman |
| 5,860,995 A | 1/1999 | Berkelaar |
| 5,873,817 A | 2/1999 | Kokish et al. |
| 5,885,299 A | 3/1999 | Winslow et al. |
| 5,891,088 A | 4/1999 | Thompson et al. |
| 5,899,914 A | 5/1999 | Zirps et al. |
| 5,928,239 A | 7/1999 | Mirza |
| 5,944,690 A | 8/1999 | Falwell et al. |
| 5,987,344 A | 11/1999 | West |
| 6,027,462 A | 2/2000 | Greene et al. |
| 6,036,682 A | 3/2000 | Lange et al. |
| 6,036,698 A | 3/2000 | Fawzi et al. |
| 6,059,739 A | 5/2000 | Baumann |
| 6,224,604 B1 | 5/2001 | Suddaby |
| 6,280,450 B1 | 8/2001 | McGuckin, Jr. |
| 6,319,257 B1 | 11/2001 | Carignan et al. |
| 6,331,166 B1 | 12/2001 | Burbank et al. |
| 6,344,026 B1 | 2/2002 | Burbank et al. |
| 6,358,251 B1 | 3/2002 | Mirza |
| 6,383,188 B2 | 5/2002 | Kuslich et al. |
| 6,423,081 B1 | 7/2002 | Lee et al. |
| 6,425,887 B1 | 7/2002 | McGuckin et al. |
| 6,440,062 B1 | 8/2002 | Ouchi |
| 6,440,138 B1 | 8/2002 | Reiley et al. |
| 6,454,727 B1 | 9/2002 | Burbank et al. |
| 6,468,279 B1 | 10/2002 | Reo |
| 6,468,289 B1 | 10/2002 | Bonutti |
| 6,482,235 B1 | 11/2002 | Lambrecht et al. |
| 6,491,681 B1 | 12/2002 | Kunis et al. |
| 6,491,689 B1 | 12/2002 | Ellis et al. |
| 6,540,693 B2 | 4/2003 | Burbank et al. |
| 6,543,455 B2 | 4/2003 | Bonutti |
| 6,547,432 B2 | 4/2003 | Coffeen et al. |
| 6,558,390 B2 | 5/2003 | Cragg |
| 6,575,978 B2 | 6/2003 | Peterson et al. |
| 6,575,979 B1 | 6/2003 | Cragg |
| 6,585,734 B2 | 7/2003 | Levinson |
| 6,592,531 B2 | 7/2003 | Bonutti |
| 6,592,559 B1 | 7/2003 | Pakter et al. |
| 6,607,534 B2 | 8/2003 | Bonutti |
| 6,626,903 B2 | 9/2003 | McGuckin, Jr. et al. |
| 6,632,231 B2 | 10/2003 | Radisch, Jr. |
| 6,647,281 B2 | 11/2003 | Morency |
| 6,652,532 B2 | 11/2003 | Bonutti |
| 6,652,548 B2 | 11/2003 | Evans et al. |
| 6,659,105 B2 | 12/2003 | Burbank et al. |
| 6,660,011 B2 | 12/2003 | Levinson |
| 6,663,588 B2 | 12/2003 | DuBois et al. |
| 6,663,602 B2 | 12/2003 | Moeller |
| 6,673,071 B2 | 1/2004 | VanDusseldorp et al. |
| 6,676,658 B2 | 1/2004 | Burbank et al. |
| 6,676,665 B2 | 1/2004 | Foley et al. |
| 6,676,668 B2 | 1/2004 | Mercereau et al. |
| 6,679,886 B2 | 1/2004 | Weikel et al. |
| 6,689,145 B2 | 2/2004 | Lee et al. |
| 6,699,206 B2 | 3/2004 | Burbank et al. |
| 6,726,690 B2 | 4/2004 | Eckman |
| 6,740,090 B1 | 5/2004 | Cragg et al. |
| 6,746,451 B2 | 6/2004 | Middleton et al. |
| 6,796,989 B2 | 9/2004 | Uflacker |
| 6,805,675 B1 | 10/2004 | Gardeski et al. |
| 6,814,734 B2 | 11/2004 | Chappuis et al. |
| 6,821,276 B2 | 11/2004 | Lambrecht et al. |
| 6,824,551 B2 | 11/2004 | Trerotola |
| 6,833,000 B2 | 12/2004 | Levinson |
| 6,835,198 B2 | 12/2004 | Bonutti |
| 6,840,944 B2 | 1/2005 | Suddaby |
| 6,849,084 B2 | 2/2005 | Rabkin et al. |
| 6,863,672 B2 | 3/2005 | Reiley et al. |
| 6,863,676 B2 | 3/2005 | Lee et al. |
| 6,875,219 B2 | 4/2005 | Arramon et al. |
| 6,899,716 B2 | 5/2005 | Cragg |
| 6,913,594 B2 | 7/2005 | Coleman et al. |
| 6,921,403 B2 | 7/2005 | Cragg et al. |
| 6,923,813 B2 | 8/2005 | Phillips et al. |
| 6,939,351 B2 | 9/2005 | Eckman |
| 6,939,352 B2 | 9/2005 | Buzzard et al. |
| 6,951,557 B2 | 10/2005 | Ellis et al. |
| 6,960,172 B2 | 11/2005 | McGuckin, Jr. et al. |
| 7,010,378 B2 | 3/2006 | Ohishi et al. |
| 7,011,670 B2 | 3/2006 | Radisch, Jr. |
| 7,014,633 B2 | 3/2006 | Cragg |
| 7,074,236 B2 | 7/2006 | Rabkin et al. |
| 7,087,058 B2 | 8/2006 | Cragg |
| 7,108,704 B2 | 9/2006 | Trerotola |
| 7,114,501 B2 | 10/2006 | Johnson et al. |
| 7,131,981 B2 | 11/2006 | Appling et al. |
| 7,134,437 B2 | 11/2006 | Bonutti |
| 7,144,397 B2 | 12/2006 | Lambrecht et al. |
| 7,153,315 B2 | 12/2006 | Miller |
| 7,172,609 B2 | 2/2007 | Radisch, Jr. |
| 7,179,024 B2 | 2/2007 | Greenhalgh |
| 7,226,481 B2 | 6/2007 | Kuslich |
| 7,234,468 B2 | 6/2007 | Johnson et al. |
| 7,241,297 B2 | 7/2007 | Shaolian et al. |
| 7,282,055 B2 | 10/2007 | Tsuruta |
| 7,291,146 B2 | 11/2007 | Steinke et al. |
| 7,309,338 B2 | 12/2007 | Cragg |
| 7,329,267 B2 | 2/2008 | Weber |
| 7,331,958 B2 | 2/2008 | Falwell et al. |
| 7,341,594 B2 | 3/2008 | Shluzas et al. |
| 7,413,568 B2 | 8/2008 | Swanson et al. |
| 7,476,226 B2 | 1/2009 | Weikel et al. |
| 7,476,244 B2 | 1/2009 | Buzzard et al. |
| 7,500,977 B2 | 3/2009 | Assell et al. |
| 7,524,301 B2 | 4/2009 | Dubois et al. |
| 7,604,611 B2 | 10/2009 | Falwell et al. |
| 7,615,044 B2 | 11/2009 | Scheibe et al. |
| 7,641,664 B2 | 1/2010 | Pagano |
| 7,658,537 B2 | 2/2010 | Coffeen et al. |
| 7,666,226 B2 | 2/2010 | Schaller |

(56) References Cited

U.S. PATENT DOCUMENTS

| | | |
|---|---|---|
| 7,666,227 B2 | 2/2010 | Schaller |
| 7,670,374 B2 | 3/2010 | Schaller |
| 7,670,375 B2 | 3/2010 | Schaller |
| 7,682,358 B2 | 3/2010 | Gullickson et al. |
| 7,682,378 B2 | 3/2010 | Truckai et al. |
| 7,686,809 B2 | 3/2010 | Triplett et al. |
| 7,699,849 B2 | 4/2010 | Eckman |
| 7,713,273 B2 | 5/2010 | Krueger et al. |
| 7,722,612 B2 | 5/2010 | Sala et al. |
| 7,749,225 B2 | 7/2010 | Chappuis et al. |
| 7,749,228 B2 | 7/2010 | Lieberman |
| 7,758,625 B2 | 7/2010 | Wu et al. |
| 7,815,650 B2 | 10/2010 | Shluzas et al. |
| 7,828,804 B2 | 11/2010 | Li et al. |
| 7,837,724 B2 | 11/2010 | Keeble et al. |
| 7,842,041 B2 | 11/2010 | Liu et al. |
| 7,846,206 B2 | 12/2010 | Oglaza et al. |
| 7,879,038 B2 | 2/2011 | Reiley et al. |
| 7,879,041 B2 | 2/2011 | Rabiner et al. |
| 7,896,880 B2 | 3/2011 | Bonutti |
| 7,909,827 B2 | 3/2011 | Reiley et al. |
| 7,935,082 B2 | 5/2011 | Datta et al. |
| 7,935,141 B2 | 5/2011 | Randall et al. |
| 7,959,642 B2 | 6/2011 | Nobis et al. |
| 7,967,789 B2 | 6/2011 | Solar et al. |
| 7,967,829 B2 | 6/2011 | Gunderson et al. |
| 7,993,301 B2 | 8/2011 | Boyd et al. |
| 7,993,384 B2 | 8/2011 | Wu et al. |
| RE42,757 E | 9/2011 | Kuslich et al. |
| 8,021,365 B2 | 9/2011 | Phan |
| 8,021,366 B2 | 9/2011 | Phan |
| 8,034,088 B2 | 10/2011 | Pagano |
| 8,052,613 B2 | 11/2011 | Assell et al. |
| 8,083,687 B2 | 12/2011 | Parihar |
| 8,090,428 B2 | 1/2012 | de Villiers et al. |
| 8,128,633 B2 | 3/2012 | Linderman et al. |
| 8,142,367 B2 | 3/2012 | Gardeski et al. |
| 8,142,441 B2 | 3/2012 | Refai et al. |
| 8,216,296 B2 | 7/2012 | Wu et al. |
| 8,226,659 B2 | 7/2012 | Rabiner et al. |
| 8,317,791 B2 | 11/2012 | Phan |
| 8,353,911 B2 | 1/2013 | Goldin et al. |
| 8,454,620 B2 | 6/2013 | Ralph et al. |
| 8,690,884 B2 | 4/2014 | Linderman et al. |
| 8,734,460 B2 | 5/2014 | Rabiner et al. |
| 8,795,306 B2 | 8/2014 | Smith et al. |
| 8,827,981 B2 | 9/2014 | Liu et al. |
| 8,894,658 B2 | 11/2014 | Linderman et al. |
| 8,986,386 B2 | 3/2015 | Oglaza et al. |
| 9,119,639 B2 | 9/2015 | Kuntz |
| 9,247,929 B2 | 2/2016 | Melsheimer |
| 9,308,001 B2 | 4/2016 | Rodriguez |
| 9,308,013 B2 | 4/2016 | Casey et al. |
| 9,389,443 B2 | 7/2016 | Takakura et al. |
| 9,504,479 B2 | 11/2016 | Nino et al. |
| 9,730,707 B2 | 8/2017 | Sasaki |
| 9,839,443 B2 * | 12/2017 | Brockman ......... A61B 17/3472 |
| 10,441,295 B2 | 10/2019 | Brockman et al. |
| 10,575,882 B2 | 3/2020 | DiPoto et al. |
| 11,191,575 B2 * | 12/2021 | Kidman ............. A61B 17/3423 |
| 11,259,818 B2 | 3/2022 | Brockman et al. |
| 11,607,258 B2 | 3/2023 | Brockman et al. |
| 2002/0016624 A1 | 2/2002 | Patterson et al. |
| 2002/0022856 A1 | 2/2002 | Johnson et al. |
| 2002/0029055 A1 | 3/2002 | Bonutti |
| 2002/0065485 A1 | 5/2002 | DuBois et al. |
| 2002/0068974 A1 | 6/2002 | Kuslich et al. |
| 2003/0191474 A1 | 10/2003 | Cragg et al. |
| 2003/0220648 A1 | 11/2003 | Osorio et al. |
| 2004/0049157 A1 | 3/2004 | Plishka et al. |
| 2004/0162559 A1 | 8/2004 | Arramon et al. |
| 2004/0267269 A1 | 12/2004 | Middleton et al. |
| 2005/0043737 A1 | 2/2005 | Reiley et al. |
| 2005/0060030 A1 * | 3/2005 | Lashinski ............. A61F 2/2466 623/2.37 |
| 2005/0075540 A1 | 4/2005 | Shluzas et al. |
| 2005/0113836 A1 | 5/2005 | Lozier et al. |
| 2005/0119662 A1 | 6/2005 | Reiley et al. |
| 2005/0182412 A1 | 8/2005 | Johnson et al. |
| 2005/0197661 A1 | 9/2005 | Carrison et al. |
| 2005/0203527 A1 | 9/2005 | Carrison et al. |
| 2005/0216018 A1 | 9/2005 | Sennet |
| 2005/0240193 A1 | 10/2005 | Layne et al. |
| 2005/0261692 A1 | 11/2005 | Carrison et al. |
| 2006/0030847 A1 | 2/2006 | McGuckin et al. |
| 2006/0085005 A1 | 4/2006 | Kenealy et al. |
| 2006/0100640 A1 | 5/2006 | Bolduc |
| 2006/0116689 A1 | 6/2006 | Albans et al. |
| 2006/0149268 A1 | 7/2006 | Truckai et al. |
| 2006/0184192 A1 | 8/2006 | Markworth et al. |
| 2006/0195106 A1 | 8/2006 | Jones et al. |
| 2006/0195107 A1 | 8/2006 | Jones et al. |
| 2006/0235338 A1 | 10/2006 | Pacheco |
| 2006/0271061 A1 | 11/2006 | Beyar et al. |
| 2007/0006692 A1 | 1/2007 | Phan |
| 2007/0010844 A1 | 1/2007 | Gong et al. |
| 2007/0021835 A1 | 1/2007 | Edidin |
| 2007/0055259 A1 | 3/2007 | Norton et al. |
| 2007/0055261 A1 | 3/2007 | Reiley et al. |
| 2007/0060933 A1 | 3/2007 | Sankaran et al. |
| 2007/0067034 A1 | 3/2007 | Chirico et al. |
| 2007/0068329 A1 | 3/2007 | Phan et al. |
| 2007/0123889 A1 | 5/2007 | Malandain et al. |
| 2007/0149990 A1 | 6/2007 | Palmer et al. |
| 2007/0198020 A1 | 8/2007 | Reiley et al. |
| 2007/0260270 A1 | 11/2007 | Assell et al. |
| 2007/0270863 A1 | 11/2007 | Melkent |
| 2007/0276392 A1 | 11/2007 | Beyar et al. |
| 2007/0282344 A1 | 12/2007 | Yedlicka et al. |
| 2007/0282345 A1 | 12/2007 | Yedlicka et al. |
| 2007/0293947 A1 | 12/2007 | Mansmann |
| 2008/0009875 A1 | 1/2008 | Sankaran et al. |
| 2008/0009876 A1 | 1/2008 | Sankaran et al. |
| 2008/0009877 A1 | 1/2008 | Sankaran et al. |
| 2008/0058827 A1 | 3/2008 | Osorio et al. |
| 2008/0114364 A1 | 5/2008 | Goldin et al. |
| 2008/0208230 A1 | 8/2008 | Chin et al. |
| 2008/0294166 A1 | 11/2008 | Goldin et al. |
| 2008/0300574 A1 | 12/2008 | Belson et al. |
| 2009/0099641 A1 | 4/2009 | Wu et al. |
| 2009/0192357 A1 | 7/2009 | Torii |
| 2009/0198272 A1 | 8/2009 | Kerver et al. |
| 2009/0210046 A1 | 8/2009 | Shumer et al. |
| 2009/0270862 A1 | 10/2009 | Arcenio |
| 2009/0270892 A1 | 10/2009 | Arcenio et al. |
| 2009/0270893 A1 | 10/2009 | Arcenio |
| 2009/0287236 A1 | 11/2009 | Bakos et al. |
| 2009/0299282 A1 | 12/2009 | Lau et al. |
| 2010/0036381 A1 | 2/2010 | Vanleeuwen et al. |
| 2010/0082033 A1 | 4/2010 | Germain |
| 2010/0145431 A1 | 6/2010 | Wu et al. |
| 2010/0160921 A1 | 6/2010 | Sun et al. |
| 2010/0211076 A1 | 8/2010 | Germain et al. |
| 2010/0241123 A1 | 9/2010 | Middleton et al. |
| 2010/0280449 A1 | 11/2010 | Alvarez et al. |
| 2010/0298832 A1 | 11/2010 | Lau et al. |
| 2011/0024145 A1 | 2/2011 | Click et al. |
| 2011/0028980 A1 | 2/2011 | Click et al. |
| 2011/0098709 A1 | 4/2011 | Malandain et al. |
| 2011/0098759 A1 | 4/2011 | Trieu |
| 2011/0184447 A1 | 7/2011 | Leibowitz et al. |
| 2011/0251615 A1 | 10/2011 | Truckai et al. |
| 2011/0264074 A1 | 10/2011 | Tegg et al. |
| 2011/0295261 A1 | 12/2011 | Germain |
| 2011/0295262 A1 | 12/2011 | Germain et al. |
| 2012/0089125 A1 | 4/2012 | Scheibe et al. |
| 2012/0130381 A1 | 5/2012 | Germain |
| 2012/0209273 A1 | 8/2012 | Zaretzka et al. |
| 2012/0239049 A1 | 9/2012 | Truckai et al. |
| 2012/0239072 A1 | 9/2012 | Rodriguez |
| 2012/0253226 A1 | 10/2012 | Parihar et al. |
| 2012/0277755 A1 | 11/2012 | Liu et al. |
| 2012/0330314 A1 | 12/2012 | Schaller et al. |
| 2013/0006232 A1 | 1/2013 | Pellegrino et al. |

(56) References Cited

U.S. PATENT DOCUMENTS

| | | |
|---|---|---|
| 2013/0012929 A1 | 1/2013 | Malkowski |
| 2013/0012958 A1 | 1/2013 | Marczyk et al. |
| 2013/0018473 A1 | 1/2013 | Cragg |
| 2013/0041403 A1 | 2/2013 | Cunningham et al. |
| 2013/0150831 A1 | 6/2013 | Griffiths |
| 2014/0018732 A1 | 1/2014 | Bagaoisan et al. |
| 2015/0011830 A1 | 1/2015 | Hunter et al. |
| 2015/0112134 A1 | 4/2015 | Suehara et al. |
| 2015/0141914 A1 | 5/2015 | Fasano et al. |
| 2015/0305797 A1 | 10/2015 | Hassoun |
| 2015/0374889 A1 | 12/2015 | Lazarus |
| 2015/0374890 A1 | 12/2015 | Lazarus |
| 2016/0006232 A1 | 1/2016 | Soulignac et al. |
| 2016/0015250 A1 | 1/2016 | Suehara |
| 2016/0074028 A1 | 3/2016 | Castro |
| 2016/0192915 A1 | 7/2016 | Papenfuss et al. |
| 2016/0228131 A1 | 8/2016 | Brockman et al. |
| 2017/0035576 A1 | 2/2017 | Schaller et al. |
| 2017/0245933 A1 | 8/2017 | Graham et al. |
| 2017/0325841 A1 | 11/2017 | Govari |
| 2018/0289436 A1 | 10/2018 | Jorgensen |
| 2018/0310982 A1 | 11/2018 | Worrell |
| 2019/0000405 A1 | 1/2019 | Shoup et al. |
| 2019/0038345 A1 | 2/2019 | Pellegrino et al. |
| 2019/0336730 A1 | 11/2019 | Cheng et al. |
| 2019/0365388 A1 | 12/2019 | Brockman et al. |
| 2020/0170738 A1 | 6/2020 | Hasegawa |
| 2021/0235969 A1 | 8/2021 | Solano Montenegro et al. |
| 2022/0110639 A1 | 4/2022 | Brockman et al. |
| 2022/0192722 A1 | 6/2022 | Harshman et al. |
| 2023/0149663 A1 | 5/2023 | Klein et al. |

FOREIGN PATENT DOCUMENTS

| | | |
|---|---|---|
| WO | 9951149 A1 | 10/1999 |
| WO | 2009155319 A1 | 12/2009 |
| WO | 2012125546 A1 | 9/2012 |
| WO | 2018218084 A2 | 11/2018 |
| WO | 2019200091 A1 | 10/2019 |

OTHER PUBLICATIONS

International Search Report for Application No. PCT/US2013/065002 dated Apr. 7, 2014, 5 pages.

International Search Report for Application No. PCT/US2020/028989 dated Nov. 6, 2020, 3 pages.

Partial International Search Report for Application No. PCT/US2020/028989 dated Sep. 16, 2020, 3 pages.

\* cited by examiner

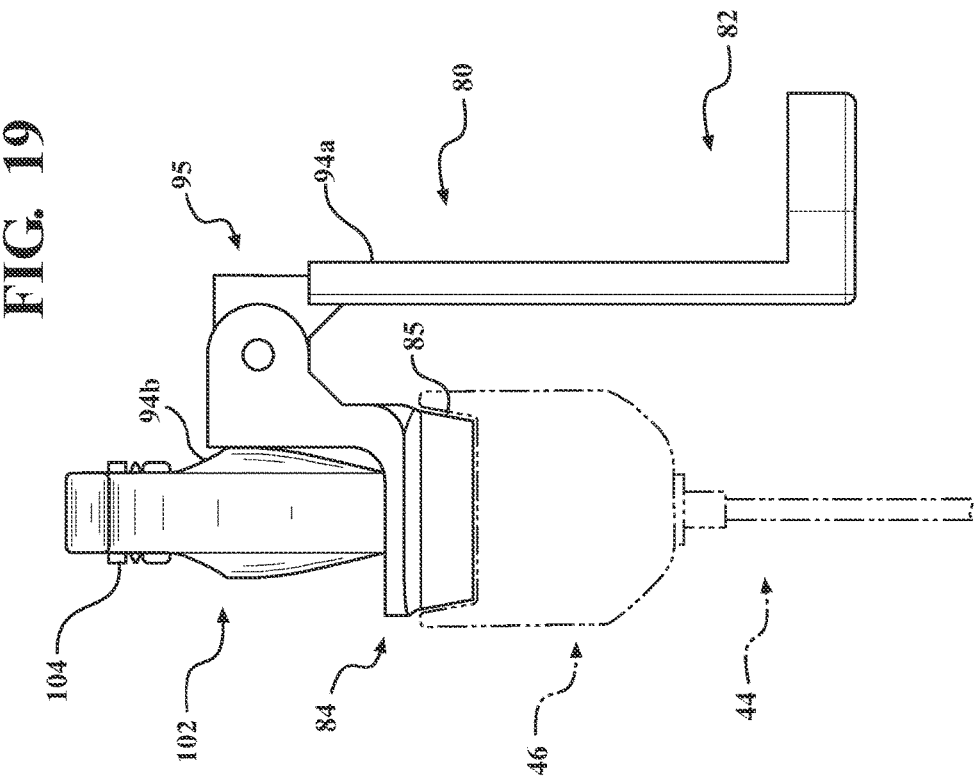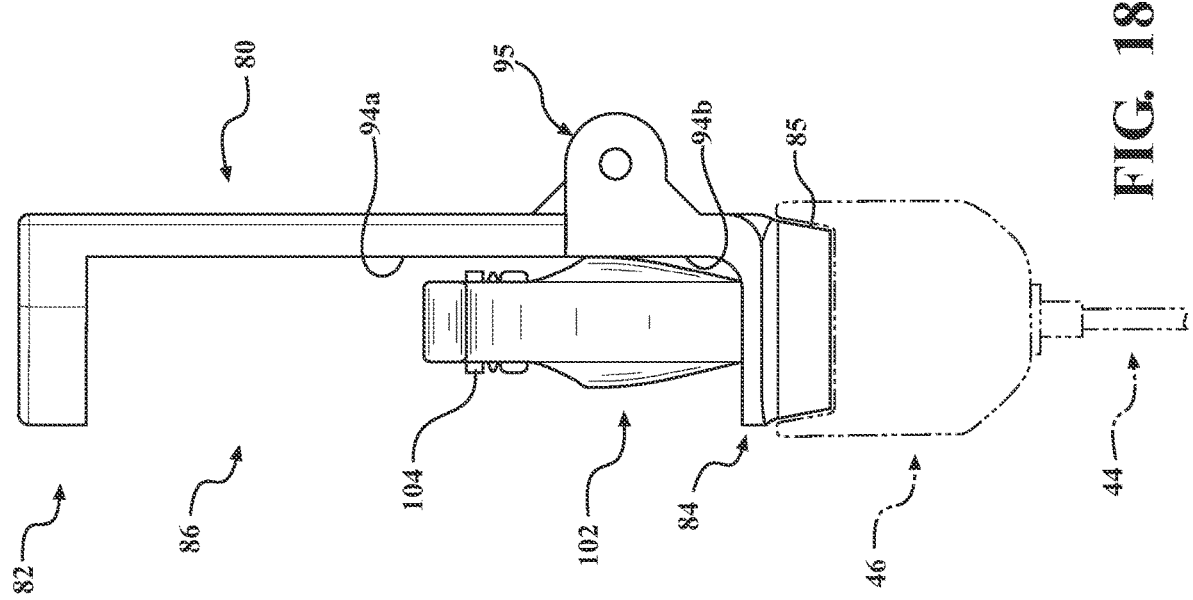

SYSTEMS AND METHODS FOR OFF-AXIS TREATMENT OF A VERTEBRAL BODY

CROSS REFERENCE TO RELATED APPLICATIONS

This is a continuation of U.S. application Ser. No. 17/603,148, filed on Oct. 12, 2021, now U.S. Pat. No. 11,849,986 which is a national entry of International Application No. PCT/US2020/028989, filed on Apr. 20, 2020, which claims priority to and all the benefits of U.S. Provisional Patent Application No. 62/837,930, filed on Apr. 24, 2019, the entire contents of each being hereby incorporated by reference.

BACKGROUND

A common source of back pain is a vertebral compression fracture in which a weakened or injured vertebral body loses height or collapses. The weakening of the vertebral body may be due to acute injury or, more often, degenerative changes such as osteoporosis. The compression fractures often appear on lateral radiographs as wedge deformities with greater loss of height anteriorly.

One treatment modality includes vertebral augmentation in which the height of the vertebral body is elevated or restored, and stabilized at the elevated or restored height. A vertebroplasty includes delivering curable material, for example a bone cement, within an interior of the vertebral body. The material interdigitates with cancellous bone and cures to stabilize the vertebral body. A kyphoplasty includes creating a cavity within the interior of the vertebral body by compressing the cancellous bone with an expandable member such as a balloon, and delivering the curable material into the cavity. The expandable member may facilitate elevating or restoring the height of the vertebral body.

Accessing the interior of the vertebral body often includes percutaneously placing an access cannula through a pedicle of the vertebra. Owing to the structure of the vertebra, accessing a location on the contralateral side of the vertebral body is not especially feasible with straight instrumentation. As such, one existing kyphoplasty technique employs a bipedicular approach in which two access cannulas are placed, followed by two balloons each positioned ipsilaterally within the interior of the vertebral body. The bipedicular approach undesirably requires twice the trauma to tissue, and often requires twice the instrumentation.

Of particular interest is a unipedicular approach in which the instrumentation is designed to access locations of the interior of the vertebral body offset from a longitudinal axis of the access cannula, including locations on the contralateral side of the vertebral body. One exemplary system utilizing the unipedicular approach is disclosed in commonly owned U.S. Pat. No. 8,894,658, issued Nov. 25, 2014, hereby incorporated by reference in its entirety, and sold under the tradename Avaflex by Stryker Corporation (Kalamazoo, Mich.). While the disclosure realizes the benefits of the unipedicular approach, there is further need in the art for systems and methods for off-axis vertebral augmentation.

SUMMARY

A first aspect of the present disclosure is directed to a system for augmenting a vertebral body. The system includes an access cannula, and introducer device, and a flexible sheath. The access cannula includes a cannula hub, and a cannula shaft extending from the cannula hub. The cannula shaft includes a distal end positionable within the vertebral body and defining a lumen along a longitudinal axis. The introducer device includes an actuator configured to receive an input from a user, and a shaft. The shaft includes a rigid proximal portion coupled to the actuator and defining a proximal end of the shaft, and a flexible distal portion. A length of the shaft between the proximal end and a distal end is sufficient for the shaft to extend through and be operable beyond the distal end of the access cannula. The flexible distal portion includes a pre-set curve in an unconstrained state. The introducer device includes a pulling element coupled to the actuator and to the shaft at or near the distal end. The pulling element extends along at least a portion of the pre-set curve. Tension on the pulling element is configured to be increased in response to the input provided to the actuator to move the pre-set curve from the unconstrained state to a constrained state in which the flexible distal portion at least partially straightens. The tension on the pulling element is configured to be reduced to facilitate the pre-set curve moving from the constrained state to the unconstrained state to position the distal end of the shaft within the vertebral body at a target site that is offset from the longitudinal axis. The flexible sheath at least partially overlying the shaft with the flexible sheath including a distal end positionable near the distal end of the shaft such that the flexible sheath is configured to extend through and be operable beyond the distal end of the access cannula with a distal portion of the flexible sheath conforming to the flexible distal portion as the pre-set curve moves between the constrained state and the unconstrained state, wherein the introducer device is removable from the flexible sheath with the distal end of the flexible sheath remaining at the target site offset from the longitudinal axis.

In some implementations, the pre-set curve defines an inner curved surface opposite an outer curved surface. The pulling element may extend along at least a portion of the outer curved surface. The introducer device may include a housing, and a locking mechanism operably coupling the housing and the actuator, wherein the locking mechanism is configured to permit selective locking of the actuator in one of a plurality of positions.

In some implementations, the system includes an expandable member assembly including a balloon hub, a balloon tube extending from the balloon hub, and a balloon coupled to a distal end of the balloon tube. The balloon hub is adapted to be coupled to a fluid source. The balloon tube may be sized to be slidably inserted within the flexible sheath. The balloon may be configured to be inflated with fluid from the fluid source to displace cancellous bone within the vertebral body. The balloon tube has a length such that the balloon is positioned proximate the distal end of the flexible sheath when the balloon tube is slidably inserted within the flexible sheath.

A second aspect of the disclosure involves a method of operating the system according to the first aspect of the disclosure, and optionally, any of its corresponding implementations.

A third aspect of the present disclosure is directed to a system for augmenting a vertebral body. The system includes an access cannula, a delivery cannula, an expandable member assembly, and a spacer hub. The access cannula includes a cannula hub, and a cannula shaft extending from the cannula hub. The cannula shaft includes a distal end positionable within the vertebral body. The delivery cannula includes a delivery hub, and a sheath extending from the delivery hub. The sheath includes a distal end opposite a proximal end collectively defining a length sufficient to extend through and be operable beyond the distal end of the access cannula. The delivery hub is movable relative to the cannula hub such that the sheath is slidably disposed within the cannula shaft. The expandable member assembly includes a balloon hub adapted to be coupled to a fluid source. A balloon tube extends from the balloon hub and is sized to be slidably inserted within the sheath. A balloon is coupled to a distal end of the balloon tube and configured to be inflated with fluid from the fluid source to displace cancellous bone within the vertebral body. The spacer hub is configured to facilitate proximal movement of the delivery cannula relative to the access cannula and the expandable member assembly. The sheath is retracted to expose the balloon within the vertebral body through a syringe-style input from a user. The spacer hub includes a distal portion engaging the cannula hub and a proximal portion for engaging the balloon hub. The distal and proximal portions include opposing stop surfaces defining a void space with the delivery hub configured to be movably disposed within the void space such that the opposing stop surfaces provide a terminus of movement of the delivery hub.

In some implementations, the system includes a biasing element operably coupled to the pulling element and the actuator. The biasing element may be configured to be at least initially in a stressed state to bias the pulling element to the constrained state. The biasing element may be further configured to relax in response to the input provided to the actuator to facilitate altering the tension on the pulling element to permit the flexible distal portion to move to the unconstrained state.

A fourth aspect of the disclosure is directed to a system for augmenting a vertebral body. The system includes an access cannula, a delivery cannula, an expandable member assembly, and a spacer hub. The access cannula includes a cannula hub, and a cannula shaft extending from the cannula hub. The cannula shaft includes a distal end positionable within the vertebral body. The delivery cannula includes a delivery hub, and a sheath extending from the delivery hub. The sheath includes a distal end opposite a proximal end collectively defining a length sufficient to extend through and be operable beyond the distal end of the access cannula. The delivery hub is movable relative to the cannula hub such that the sheath is slidably disposed within the cannula shaft. The expandable member assembly includes a balloon hub adapted to be coupled to a fluid source. A balloon tube extends from the balloon hub and sized to be slidably inserted within the sheath. A balloon is coupled to a distal end of the balloon tube and configured to be inflated with fluid from the fluid source to displace cancellous bone within the vertebral body. The spacer hub is configured to facilitate proximal movement of the delivery cannula relative to the access cannula and the expandable member assembly. The sheath is retracted to expose the balloon within the vertebral body through a syringe-style input from a user. The spacer hub includes a distal portion engaging the cannula hub, a proximal portion configured to engage the balloon hub, and a pivot pivotably coupling the distal portion to the proximal portion.

In some implementations, the balloon hub includes a body portion, a transition surface configured to engage the proximal portion of the spacer hub, and a control surface opposite the transition surface and sized to receive a thumb of the user to facilitate providing the syringe-style input. The delivery hub may define a lumen and each of the distal and proximal portions of the spacer hubs define coaxial apertures. At least a portion of the balloon tube may extend through the lumen and the coaxial apertures such that the delivery hub is slidable along the balloon tube between the distal and proximal portions of the spacer hub. At least one side may extend between the distal and proximal portions. The side(s) may be two sides defining opposed slots extending between the distal and proximal portions. The delivery hub comprises wings extending through the opposed slots and configured to receive the syringe-style input from the user.

In some implementations, the spacer hub includes a pivot pivotably coupling the distal portion and the proximal portion. The delivery hub may include a coupler defining an opening in communication with the sheath, wherein pivoting the proximal portion relative to the distal portion exposes the coupler for removably coupling a cement delivery system with the coupler.

In some implementations, the spacer hub is configured to be operable with the system according to the first aspect of the present disclosure, and optionally, any of its corresponding implementations.

A fourth aspect of the disclosure involves a method of operating the system according to the third aspect of the disclosure, and optionally, any of its corresponding implementations.

A fifth aspect of the disclosure is directed to a system for augmenting a vertebral body. The system includes an access cannula and an instrument. The access cannula includes a cannula shaft includes a distal end positionable within the vertebral body that defines a lumen along a longitudinal axis. A cannula hub includes a shaft hub rigidly coupled to the cannula shaft, and a tuning hub movably coupled to the shaft hub. The shaft hub is at a fixed distance from the vertebral body when the distal end of the cannula shaft is positioned within the vertebral body to provide a datum. The tuning hub includes an interference surface movable relative to the shaft hub between plurality of supported positions. The instrument includes an elongate member slidably disposed within the lumen of the cannula shaft and includes a length defined between proximal and distal ends being sufficient for the elongate member to extend through and be operable beyond the distal end of the access cannula. An instrument hub is coupled to the proximal end of the elongate member. The cannula hub is configured to be engaged by the instrument hub to prevent distal movement of the instrument relative to the access cannula while permitting proximal movement of the instrument relative to the access cannula. The movement of the tuning hub relative to the shaft hub to one of the plurality of supported positions facilitates selective adjustment of an axial position of the interference surface of the tuning hub relative to the datum.

In some implementations, each of the shaft hub and the tuning hub may include complementary threading for permitting the selective adjustment of the interference surface through a twisting input from the user. Each of the shaft hub and the tuning hub may define apertures coaxially aligned with the lumen with at least one of the instrument hub and the elongate member extending through the coaxial apertures. The instrument may be one of an introducer device, a delivery cannula, and an expandable member assembly.

In some implementations, the instrument hub is configured to be operable with the systems according to the first and third aspects of the present disclosure, and optionally, any of their corresponding implementations.

A sixth aspect of the disclosure is directed to a method of operating the system according to the fifth aspect of the disclosure, and optionally, any of its corresponding implementations.

A seventh aspect of the disclosure is directed to a system for augmenting a vertebral body. The system includes an access cannula, an introducer device, and a flexible sheath. The access cannula include includes a distal end positionable within the vertebral body and defining a lumen along a longitudinal axis. The introducer device includes a shaft coupled to the actuator. The shaft includes a rigid proximal portion coupled to the actuator and defining a proximal end of the shaft, and a flexible distal portion at or near a distal end opposite the proximal end with a length of the shaft between the proximal and distal ends being sufficient for the shaft to extend through and be operable beyond the distal end of the access cannula. The flexible distal portion is configured to move between a curved configuration to a target site within the vertebral body that is offset from the longitudinal axis, and a straightened configuration for insertion of the flexible distal portion and the flexible sheath through the lumen of the access cannula. The flexible sheath overlies the shaft with the flexible sheath includes a distal end positionable near the distal end of the shaft. The flexible sheath is configured to extend through and be operable beyond the distal end of the access cannula. At least a distal portion of the flexible sheath configured to conform to the flexible distal portion as the flexible distal portion moves between the curved configuration and the straightened configuration. At least two radiopaque markers are disposed on the distal portion of the flexible sheath and spaced apart from one another. As the distal portion is curved within the vertebral body, relative positions between the at least two radiopaque markers is viewable on radiography to determine a curvature of the curve.

In some implementations the radiopaque markers are exactly two radiopaque markers. The radiopaque markers may be one of dots, bands, rings, and lines.

In some implementations, the radiopaque markers are configured to be operable with the systems according to the first, third, fifth and seventh aspects of the present disclosure, and optionally, any of their corresponding implementations.

An eighth aspect of the disclosure is directed to a method of operating the system according to the seventh aspect of the disclosure, and optionally, any of its corresponding implementations.

BRIEF DESCRIPTION OF THE DRAWINGS

Advantages of the present invention will be readily appreciated as the same becomes better understood by reference to the following detailed description when considered in connection with the accompanying drawings.

FIG. 18 is an elevation view of the spacer hub of FIG. 17 in the first position. The access cannula and a delivery cannula including the flexible sheath are shown in phantom.

FIG. 19 is an elevation view of the spacer hub of FIG. 17 in a second position. The access cannula and a delivery cannula including the flexible sheath are shown in phantom.

DETAILED DESCRIPTION

Figure 1:
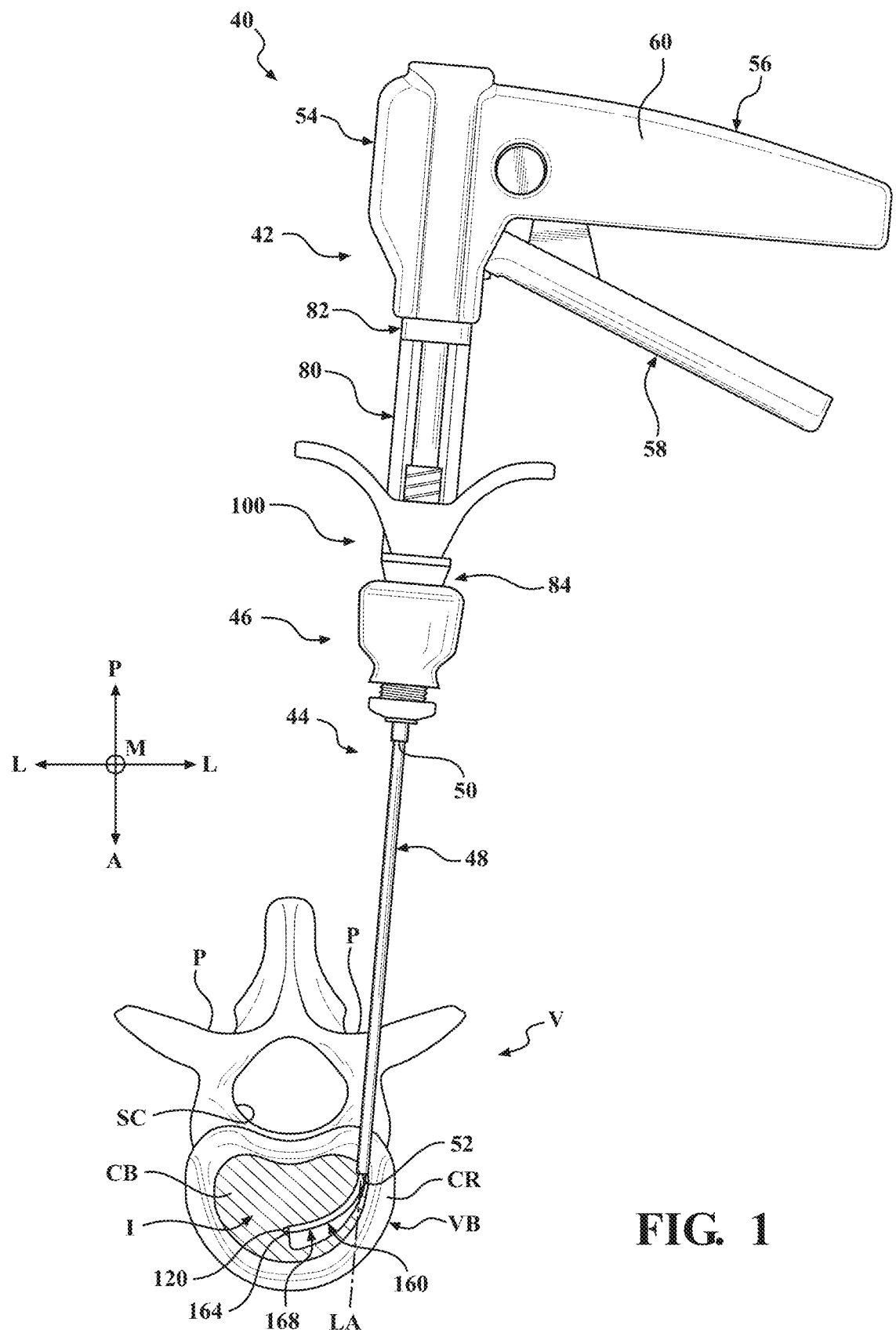
FIG. 1 shows a system for augmenting a vertebral body. An access cannula is directed through a pedicle of the vertebra, and an introducer device and a flexible sheath extend through the access cannula. A pre-set curve of a shaft of the introducer device is in an unconstrained state within the vertebral body.

FIG. 1 shows a system 40 for augmenting a vertebral body. An illustration of an axial section of a vertebra (V) is shown with certain structures and regions to be referenced throughout the present disclosure. The vertebra (V) includes pedicles (P) on opposing lateral sides of a spinal canal (SC) that provide a generally linear path from a posterior approach to an interior (I) region of the vertebral body (VB). The vertebral body (VB) includes a cortical rim (CR) formed from cortical bone that at least partially defines the interior (I) region. A volume of cancellous bone (CB) is within the interior (I) region. With reference to the compass rose of FIG. 1, the anatomical directions may also be referenced in accordance with standard medical convention; i.e., medial (M) to the center of the body, lateral (L) to the sides of the body, anterior (A) to the front of the body, and posterior (P) to the rear of the body.

The system 40 includes an introducer device 42 and an access cannula 44. The access cannula 44 includes a cannula hub 46, and a cannula shaft 48 extending from the cannula hub 46. The cannula shaft 48 includes a proximal end 50 coupled to the cannula hub 46, and a distal end 52 opposite the proximal end 50. The cannula shaft 48 may be straight and define a lumen (not identified) extending between the proximal and distal ends 50, 52 such that the cannula shaft 48 is tubular in shape. The cannula shaft 48 may be formed from biocompatible materials with sufficient mechanical properties to maintain integrity as the cannula shaft 48 is driven through the pedicle of the vertebra. The system 40 may include a trocar (not shown) removably positioned within the cannula shaft 48 during placement of the distal end 52 of the cannula shaft 48 into the vertebral body. The trocar may include a length slightly greater than a length of the cannula shaft 48 such that a sharp tip of the trocar pierces the cortical bone of the cortical rim, and the trocar prevents coring of tissue within the lumen of the cannula shaft 48. Once the distal end 52 of the cannula shaft 48 is positioned within the vertebral body, for example as shown in FIG. 1, the trocar is removed. The access cannula 44 provides a working channel to within the interior region of the vertebral body along a longitudinal axis (LA) defined by the cannula shaft 48. The cannula hub 46 is exposed above the tissue overlying the vertebra, and configured to be engaged by the introducer device 42.

Figure 2:
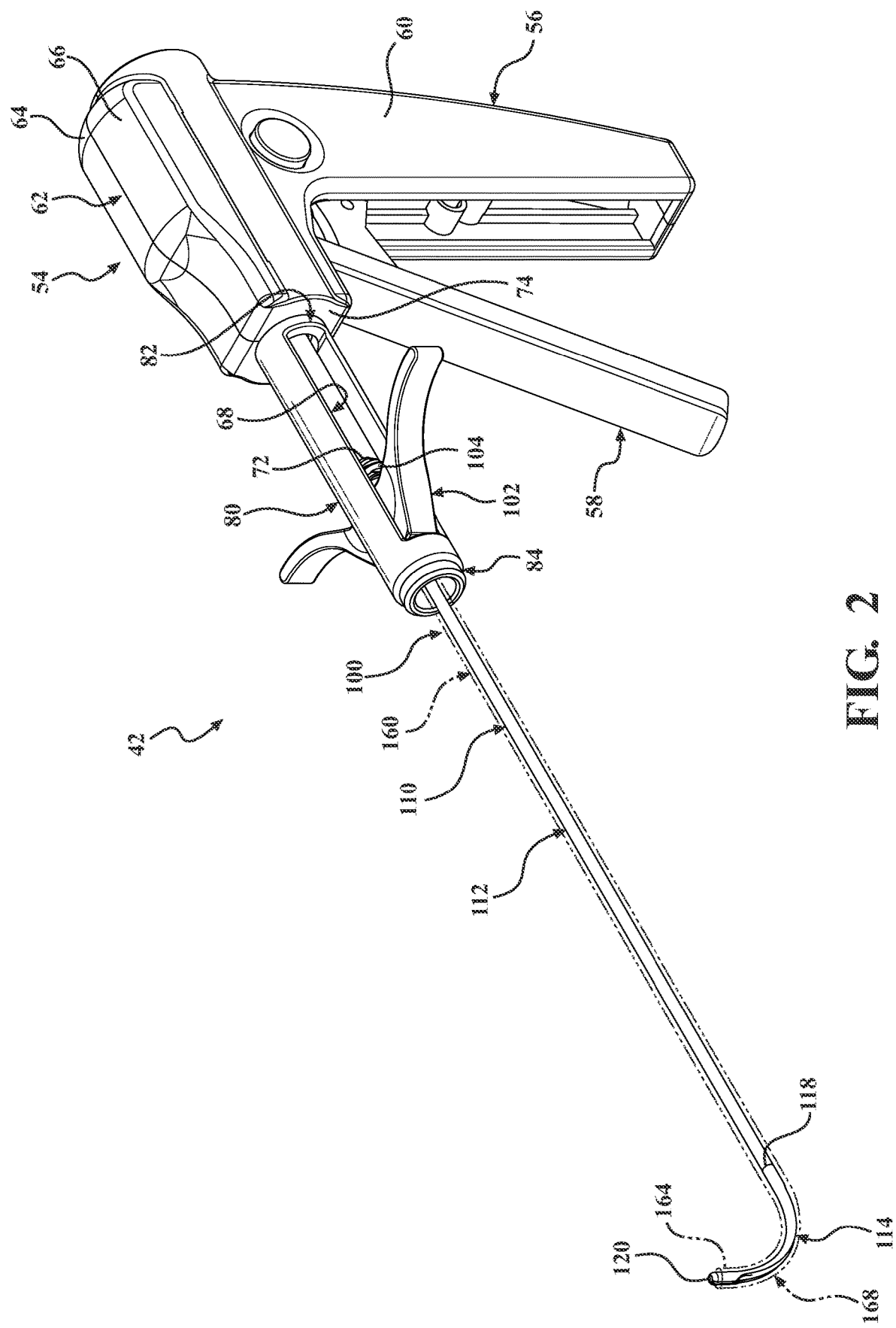
FIG. 2 is a front perspective view of the introducer device. The flexible sheath is shown in phantom.
Figure 3:
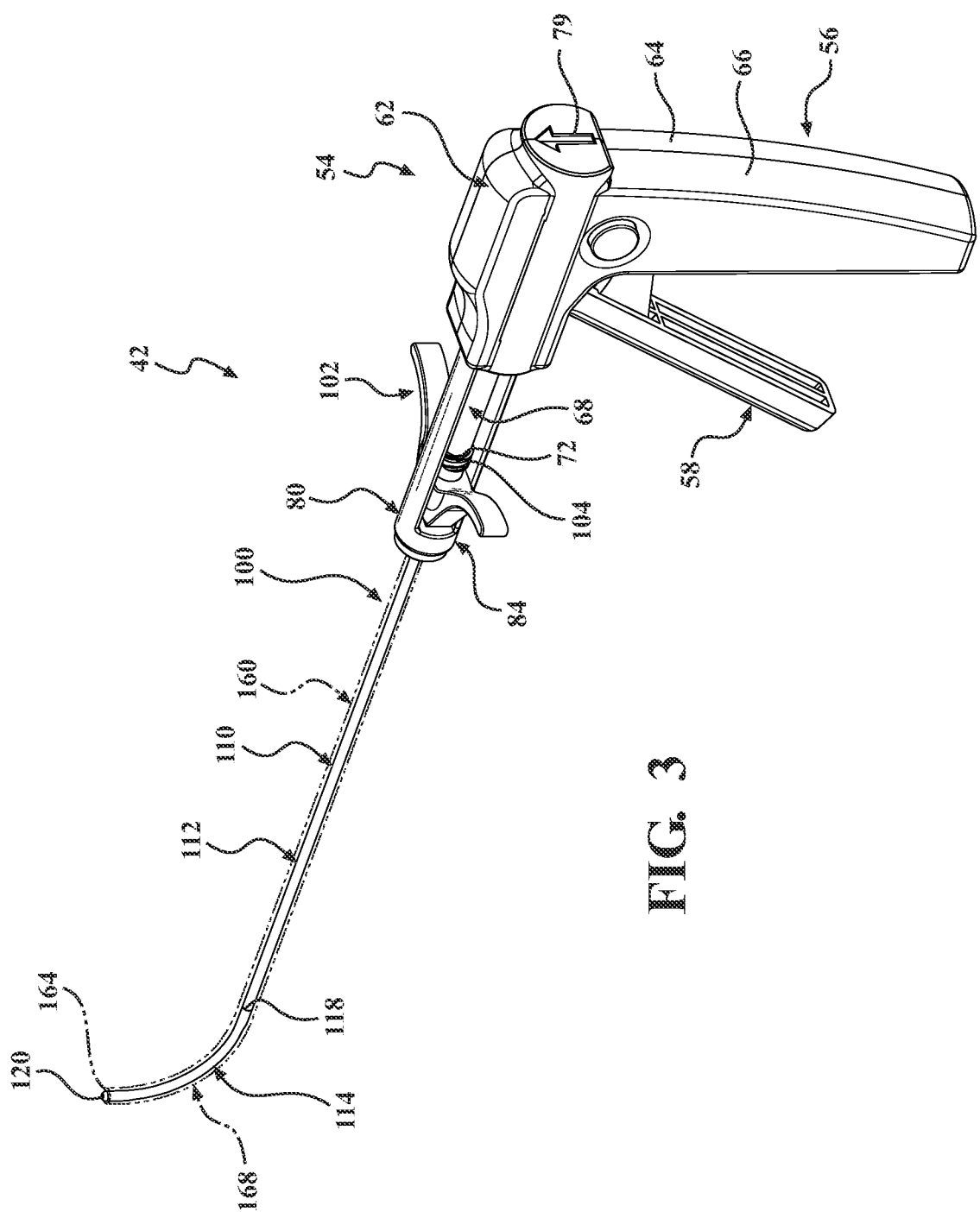
FIG. 3 is a rear perspective view of the introducer device of FIG. 2.

With further reference to FIGS. 2 and 3, the introducer device 42 includes an actuator 54. The actuator 54 is configured to receive an input from a practitioner or user to actuate the introducer device 42 in a manner to be further described. The actuator 54 includes a housing 56, and a control surface 58 movably coupled to the housing 56. FIGS. 1-3 show the housing 56 and the control surface 58 in a "pistol-grip" arrangement in which a handle 60 of the housing 56 is configured to rest in a palm of a hand of the practitioner, and the control surface 58 configured to be pulled towards or released away from the handle 60 with one or more fingers of the hand of the practitioner. Other arrangements of the actuator 54 are contemplated, for example a rotary knob disclosed in commonly owned United States Patent Publication No. 2016/0228131, filed Apr. 13, 2016, the entire contents of which are hereby incorporated by reference. The housing 56 also includes a frame 62 coupled to the handle 60. FIGS. 1-3 show the frame 62 integrally formed with the handle 60 in a generally L-shaped arrangement. The housing 56 may be formed from mirrored housing shells 64, 66 joined together, which be manufactured from polymers, metals, composites, and combinations thereof. For example, each of the housing shells 64, 66 may be injection molded so as to be low cost and disposable after a single use. The housing shells 64, 66 may at least partially define an interior of the housing 56 sized and shaped to accommodate several components of the actuator 54 to be described.

The housing 56 may further include a barrel 68 extending distal to (or forward of) the frame 62. As used herein, distal or distally refers to a direction away from the practitioner, and proximal or proximally refers to a direction towards the practitioner. The barrel 68 defines a bore in communication with the interior of the housing 56. A distal end 70 of the barrel 68 may define a distal end of the actuator 54, and a proximal end 72 of the barrel 68 may be defined by a transition surface 74 extending radially from the barrel 68. FIGS. 1 and 2 show the barrel 68 being cylindrical in shape between the proximal and distal ends 70, 72 and having an outer diameter sized to be slidably and removably inserted through a proximal portion 82 of a spacer hub 80 to be described. With the transition surface 74 engaging the proximal portion 82 of the spacer hub 80, as best shown in FIG. 2, a length of the barrel 68 defined between the proximal and distal ends 70, 72 may be sufficient to engage or abut a coupler 104 of a delivery cannula 100. The engagement of the distal end 70 of the barrel 68 with the coupler 104 of the delivery cannula 100 prevents premature proximal movement of the delivery cannula 100 while the introducer device 42 is being placed within the vertebral body through the access cannula 44.

Figure 4:
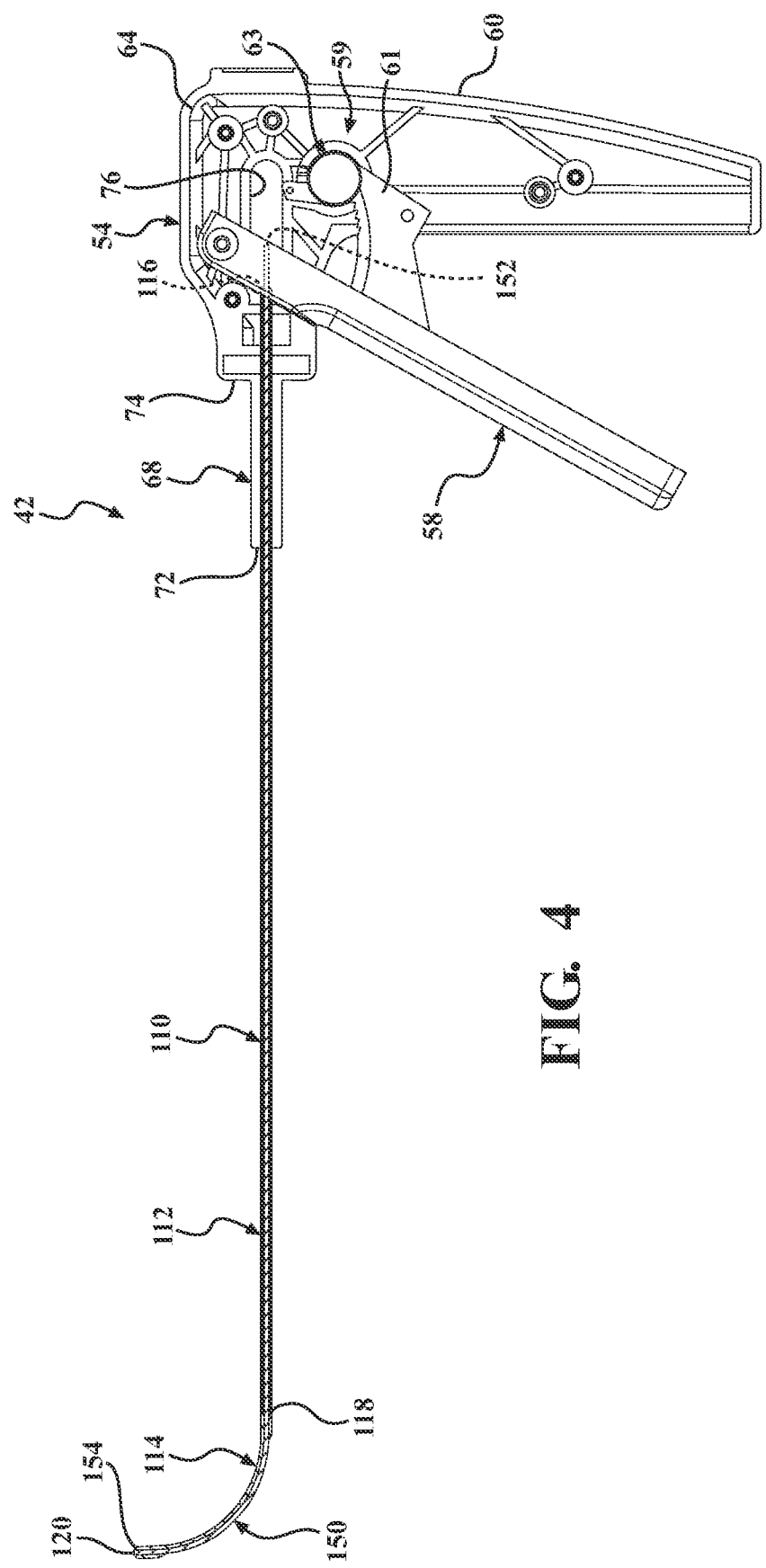
FIG. 4 is a sectional view of the introducer device of FIG. 2 with the pre-set curve of the shaft shown in an unconstrained state.
Figure 5:
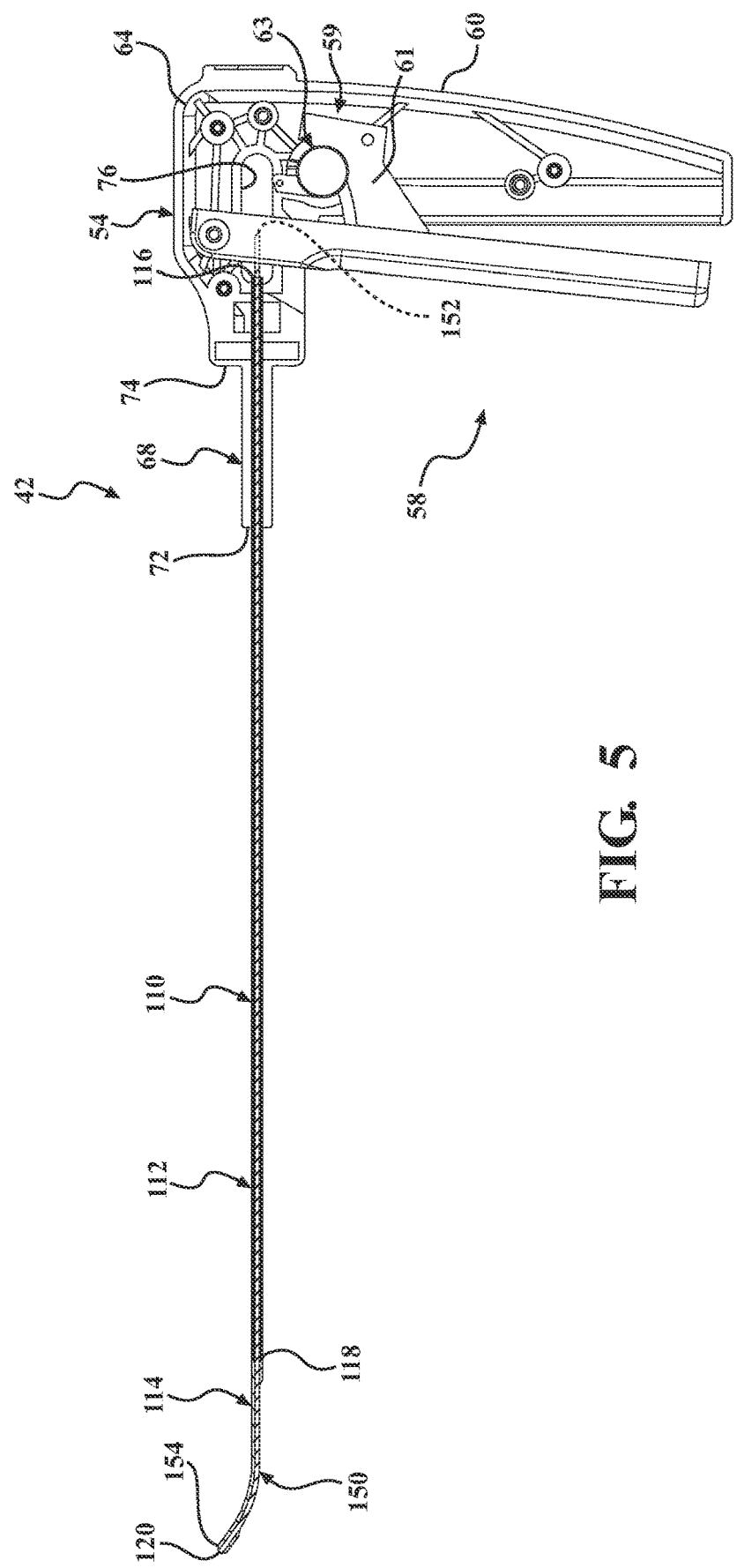
FIG. 5 is another sectional view of the introducer device with the pre-set curve of the shaft shown in a constrained state.

The introducer device 42 includes a shaft 110 coupled to the actuator 54, and more particularly to the frame 62 of the handle 60. The shaft 110 includes a rigid proximal portion 112 and a flexible distal portion 114. FIGS. 4 and 5 show the proximal portion 112 of the shaft 110 extending through the bore of the barrel 68 to a position within the interior of the handle 60. The proximal portion 112 of the shaft 110 may be axially and rotationally fixed relative to the actuator 54. The proximal portion 112 may be defined between a proximal end 116 of the shaft 110, and an interface 118 between the proximal and distal portions 112, 114 of the shaft 110. The distal portion 114 may be defined between the interface 118 and a distal end 120 of the shaft 110 opposite the proximal end 116. A length of the shaft 110 may be defined between the proximal and distal ends 116, 120 with the length being sufficient for the shaft 110 to extend through and be operable beyond the distal end 52 of the access cannula 44 as shown in FIG. 1. As such, the introducer device 42 is configured to be directed through the access cannula 44 to locations within the interior region of the vertebral body.

The proximal portion 112 may include rigid material(s) with sufficient mechanical properties to avoid more than minimal flexure. Further, the proximal portion 112 may define a lumen 121 extending between the proximal end 116 of the shaft 110 and the interface 118 such that the proximal portion 112 is tubular in shape with the tubular geometry contributing to its relatively greater stiffness than the geometry of the distal portion 114. In particular and with further reference to FIGS. 6 and 7, the distal portion 114 may include a proximal segment 122, a distal segment 124, and a flexing region 126 between the proximal and distal segments 122, 124. The proximal segment 122 includes a boss 128 disposed within a complementary bore 130 of the proximal portion 112 of the shaft 110. The engagement of the boss 128 and the bore 130 defines the interface 118 joining the proximal and distal portions 112, 114 of the shaft 110, and the joining may be facilitated through brazing, welding, adhesive, or other suitable joining process. The proximal segment 122 distal to the boss 128 may be tubular in shape with an outer diameter equal to that of the proximal portion 112 of the shaft 110 to provide a smooth transition across the interface 118. The distal segment 124 may also be tubular in shape with an outer diameter equal to that of the proximal segment 122. The distal segment 124 defines a channel 132 sized to receive a pulling element 150 of the introducer device 42 to be described.

The flexing region 126 includes a pre-set curve in an unconstrained state to define an inner curved surface 134 opposite an outer curved surface 136. More particularly, a taper 138, 140 at each of the opposing ends of the flexing region 126 define transitions from the flexing region 126 to the proximal and distal segments 122, 124. The tapers 138, 140 extend radially inward to form a cavity 142 in communication with the lumen 121 of the proximal portion 112. In other words, the cavity 142 may be considered an axial bifurcation of a curved segment of a tubular structure. The outer curved surface 136 may define a portion of the cavity 142, and the inner curved surface 134 may appear as a smooth transition between the proximal and distal segments 122, 124 such that the inner curved surface 134 is somewhat convex-concave in geometry. The cavity 142 results in the flexing region 126 being thin in thickness along its length (relative to width), the flexing region 126 is configured to flex or bend about its minor axis between, for example, the configurations shown in FIGS. 4 and 5.

Figure 6:
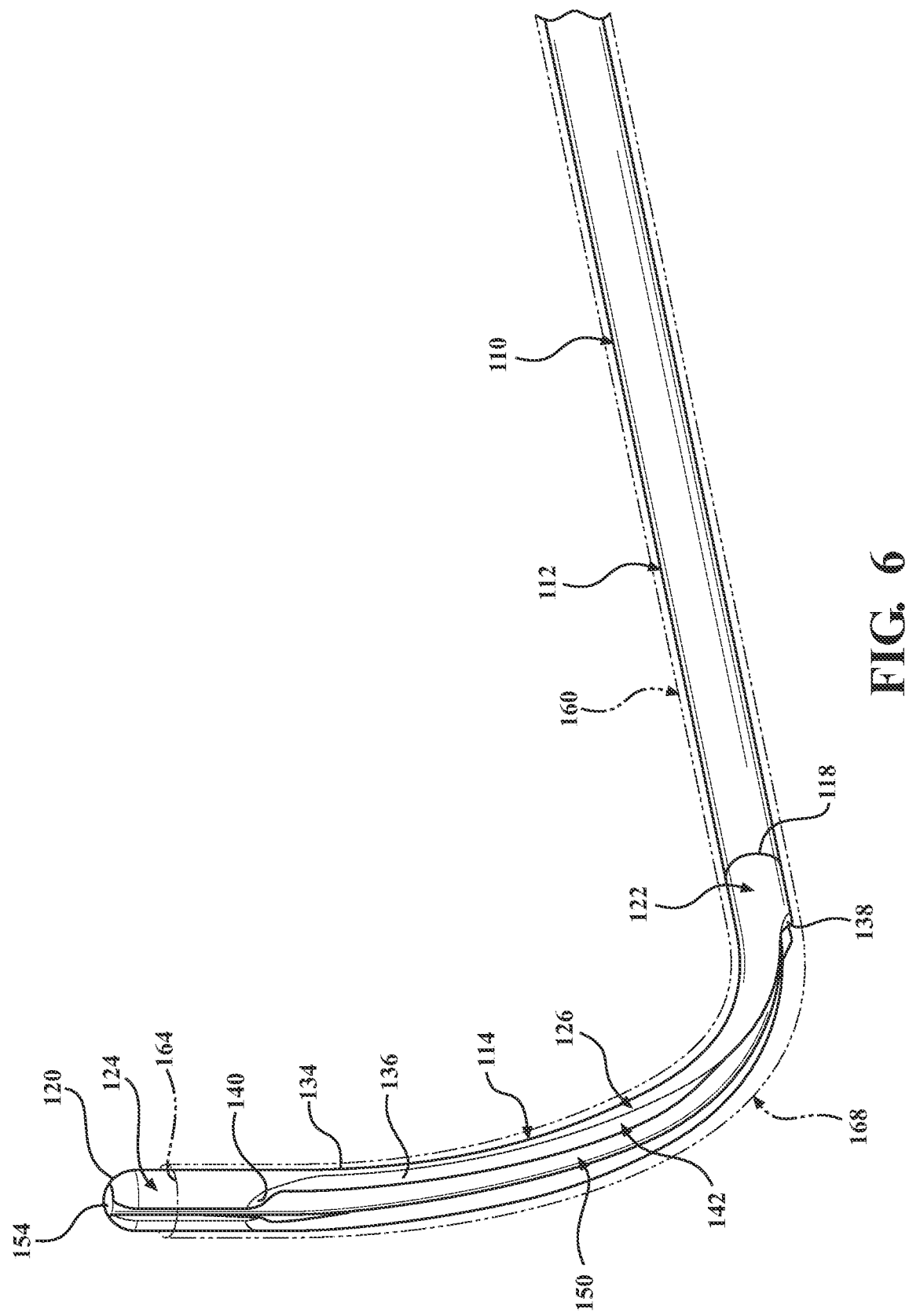
FIG. 6 is a perspective view of a portion of the shaft of the introducer device with a portion of the flexible sheath shown in phantom.
Figure 7:
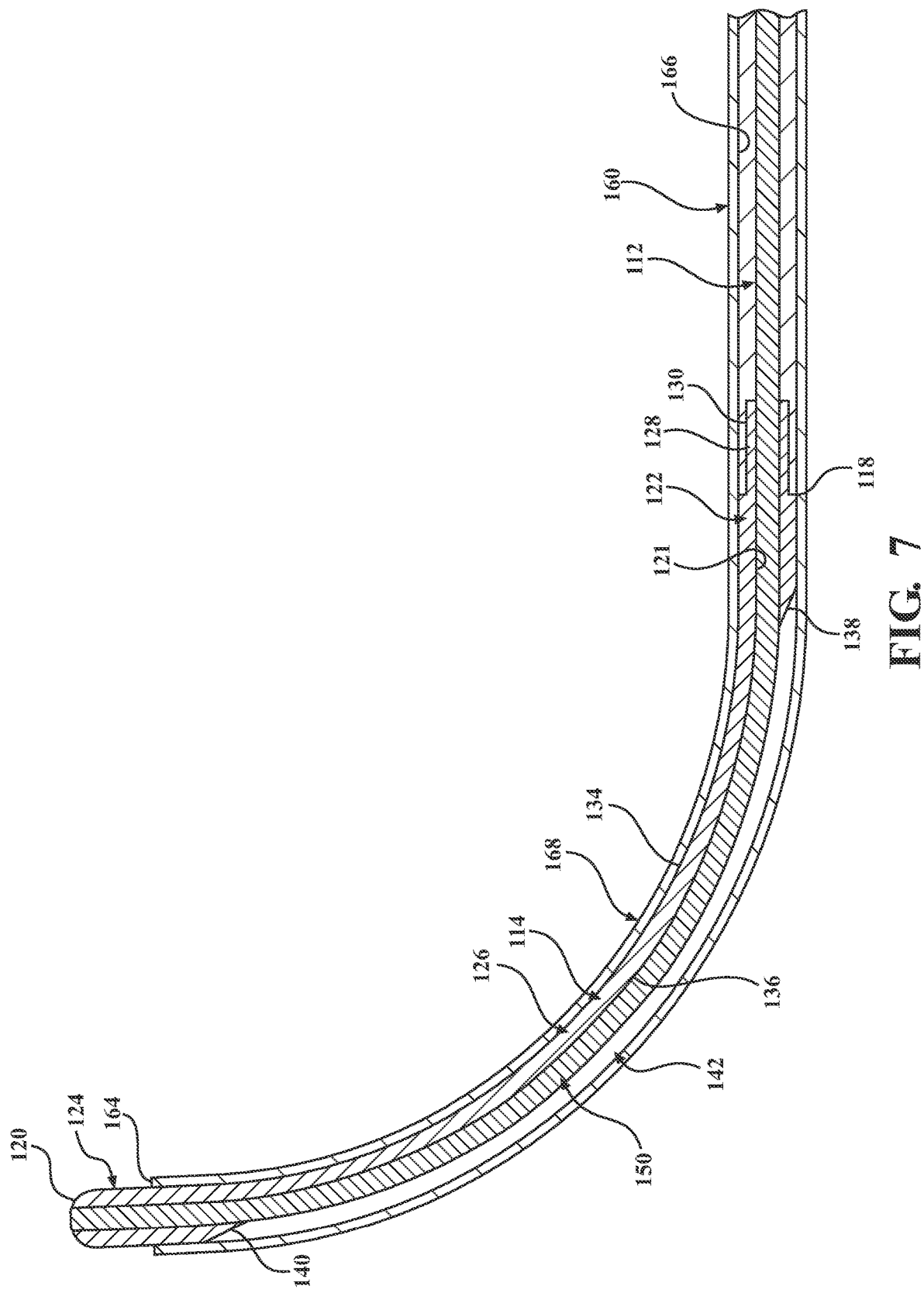
FIG. 7 is a sectional view of the portion of the shaft and the flexible sheath of FIG. 6.

The distal portion 114, and more particularly at least the flexing region 126, may include a superelastic shape memory material such as a nickel titanium alloy (i.e., Nitinol). The superelastic shape memory material is formed to assume the pre-set curve such that, in the unconstrained state, the superelastic shape memory material moves the distal portion 114 of the shaft 110 upwardly away from the proximal portion 112 of the shaft 110. For example, FIGS. 6 and 7 show the distal portion 114 oriented at an angle of approximately 90 degrees relative to the proximal portion 112. It is contemplated that the pre-set curve may be designed within the range of approximately 50 to 150 degrees, and more particularly within the range of approximately 65 to 125 degrees, and even more particularly within the range of approximately 80 to 100 degrees. As to be described in greater detail, when the introducer device 42 is directed through the access cannula 44, the pre-set curve facilitates positioning the distal end 120 of the shaft 110 at a location within the vertebral body that is offset from the longitudinal axis.

The introducer device 42 includes the pulling element 150 coupled to the actuator 54 and the shaft 110. The pulling element 150 is configured to be selectively tensioned to alter the extent of the pre-set curve. With continued reference to FIGS. 4-7, the pulling element 150 includes a proximal end 152 coupled to the actuator 54, and more particularly the control surface 58 of the actuator 54. The pulling element 150 may extend through an aperture (not identified) in the control surface 58 and secured proximal to the control surface 58 with an interference connector 78, for example a ferrule, nut, swaged sleeve, clamp, or other suitable connector. The connector 78 may be sized to movably ride within a slot defined by complementary pockets 76 in each of the housing shells 64, 66 (one identified in FIGS. 4 and 5). An input to the control surface 58 (e.g., pulled towards the handle 60) urges the connector 78 proximally within the slot, thereby tensioning the pulling element 150.

The pulling element 150 includes a distal end 154 opposite the proximal end 152 coupled at or near the distal end 120 of the shaft 110. As best shown in FIGS. 6 and 7, the pulling element 150 extends through the lumen 121 of the proximal portion 112 of the shaft 110, along the outer curved surface 136 of the flexing region 126, and through the channel 132 of the distal segment 124. The distal end 154 may be coterminous with the distal end 120 of the shaft 110. The distal end 154 of the pulling element 150 may be joined at or near the distal end 120 of the shaft 110 through brazing, welding, adhesive, interference fit, or other suitable joining process. The pulling element 150 may be monolithic in construction and formed from a metal, polymer, composite, or combination thereof. For example, the pulling element 150 may be a wire rope, a wire, a rod, and the like, of solid or hollow construction.

The flexing region 126 includes the pre-set curve in the unconstrained state, which may include minimal or zero tension being exerted on the pulling element 150. It should be appreciated that some tension may be on the pulling element 150 in the unconstrained state. In the unconstrained state, the distal portion 114 of the shaft 110 is oriented, curved, bent, or angled relative to the proximal portion 112 of the shaft 110, as shown in FIGS. 4, 6 and 7. As mentioned, the input to the control surface 58 increases the tension on the pulling element 150 to move the pre-set curve to a constrained state in which the distal portion 114, and more particularly the flexing region 126, at least partially straightens. The constrained state may include more tension being exerted on the pulling element 150 than the unconstrained state. FIG. 5 shows the pre-set curve in one example of the constrained state. In a manner to be described, moving the pre-set curve to the constrained state may be indicated for directing the introducer device 42 through and/or removing the introducer device 42 from the access cannula 44.

With the pre-set curve in the constrained state, the superelastic shape memory material of the distal portion 114 stores potential energy. Upon releasing of the input to the control surface 58, the potential energy stored by the superelastic shape memory material is sufficient to overcome the tension on the pulling element 150 no longer constrained by the input. In other words, releasing the input to the control surface 58 relaxes (i.e., reduces the tension on) the pulling element 150, and the pre-set curve moves from the constrained state to the unconstrained state in which the distal portion 114 of the shaft 110 orients, curves, bends, or angles relative to the proximal portion 112 of the shaft 110 to a greater extent than the constrained state. With the distal portion 114 within the vertebral body, the pre-set curve moving from the constrained state to the unconstrained state may displace cancellous bone within the vertebral body, and/or position the distal end 120 of the shaft 110 at a target site that is offset from the longitudinal axis, as shown in FIG. 1. A direction of the orientation, curve, bend, or angle may correlate to indicia 79 disposed on a proximal side of the actuator 54, and more particularly the frame 62, thereby visible to the practitioner.

The actuator 54 may include a locking mechanism 59 operably coupling the housing 56 and the control surface 58 and configured to permit selective locking of the control surface 58 in one of a plurality of positions. FIGS. 4 and 5 show one possible implementation of the locking mechanism 59 as a ratchet including a rack 61 coupled to the control surface 58 configured to engage a pawl 63 coupled to the housing 56. The rack 61 is shown as a protrusion extending proximally from the control surface 58 with a plurality of teeth disposed along an arcuate surface. The pawl 63 may be a cross-member extending between the housing shells 64, 66 and including an edge configured to releasably engage one of the plurality of teeth of the rack 61. Each of the teeth may correspond to one of the plurality of positions in which the control surface 58 may be locked relative to the housing 56. Actuating the locking mechanism 59 to lock the control surface 58 maintains the tension on the pulling element 150, and consequently an extent of the constrained state of the pre-set curve in the plurality of positions. Other possible constructions of the locking mechanism are contemplated.

The introducer device 42 includes the delivery cannula 100, and the delivery cannula 100 includes a delivery hub 102, the coupler 104 on the delivery hub 102, and a flexible sheath 160 extending from the delivery hub 102. The sheath 160 overlies the shaft 110 of the introducer device 42 and, in manners to be further described, performs several functions of the vertebral augmentation, for example, providing a pathway for positioning of a balloon 206 and/or for the delivery of the curable material. The sheath 160 includes a proximal end 162 (see FIG. 15) coupled to the delivery hub 102, and a distal end 164 opposite the proximal end 162 and configured to be positioned at or near the distal end 120 of the shaft 110. As best shown in FIGS. 6 and 7, the distal end 164 of the sheath 160 is slightly proximal to the distal end 120 of the shaft 110. The sheath 160 may be tubular in shape and define a lumen 166 sized to slidably and snugly receive the shaft 110 and the pulling element 150. Owing to the presence of the cavity 142 of the flexing region 126, a slight gap may exist within the lumen 166 between the sheath 160 and the outer curved surface 136 of the distal portion 114 of the shaft 110. A length of the sheath 160 defined between the proximal and distal ends 162, 164 may be sufficient for the sheath 160 to extend through and be operable beyond the distal end 52 of the access cannula 44, as shown in FIG. 1.

The sheath 160 is flexible and configured to conform to the shaft 110, and more particularly to the distal portion 114 of the shaft 110. The sheath 160 may be formed from a flexible biocompatible polymer having sufficient hoop strength such that the lumen 166 remains patent upon removal of the introducer device 42 from the sheath 160. Suitable flexible polymers include polypropylene, polyether ether ketone (PEEK), and the like. The sheath 160 may be formed from a flexible biocompatible metal, composite, and combinations thereof, with or without reinforcing features such as filament windings or braids. At least a distal portion 168 of the sheath 160 is configured to conform to the distal portion 114 of the shaft 110 as the pre-set curve is in the constrained state for insertion of the distal portion 114 and the distal portion 168 of the sheath 160 through the lumen of the access cannula 44 to within the vertebral body, and further configured to conform to the distal portion 114 of the shaft 110 as the pre-set curve is moved from the constrained state to the unconstrained state. FIG. 1 shows the pre-set curve in the unconstrained state with the distal portion 114 of the sheath 160 conforming to the distal portion 114 of the shaft 110.

The introducer device 42 is removable from the sheath 160 with the distal end 164 of the sheath 160 remaining positioned at the target site offset from the longitudinal axis. As a result, the aforementioned pathway(s) are achievable to contralateral locations within the vertebral body. The pathway(s) facilitate the remaining steps of the vertebral augmentation procedure to be described.

Additionally or alternatively, the vertebra augmentation procedure may include directing an electrode assembly through the sheath 160 with the distal portion 114 of the sheath 160 remaining curved. One exemplary electrode assembly that is sufficiently flexible for navigating the curved distal portion 114 is described in United States Patent Publication No. 2013/0006232, published Jan. 3, 2013, the entire contents of which are hereby incorporated by reference. The electrode assembly may be bipolar or monopolar. It is contemplated that the electrode assembly may be irrigated such that a fluid is infused into the adjacent tissue prior to and/or during ablation. It is further contemplated that the electrode assembly may be cooled, for example, by circulating a fluid within pathways internal to the electrode assembly. With the electrode assembly being deployed contralaterally, procedures such as intraosseous tumor ablation, basivertebral denervation, and the like, are achievable through a unipedicular approach.

Additionally or alternatively, the vertebra augmentation procedure may include deploying an implant through the sheath 160 with the distal portion 114 of the sheath 160 remaining curved. One exemplary implant is described in commonly-owned U.S. Pat. No. 7,846,206, issued Dec. 17, 2010, and commonly-owned U.S. Pat. No. 8,986,386, issued Mar. 24, 2015, the entire contents of each are hereby incorporated by reference. It is further contemplated that the implant may include an intervertebral spacer (i.e., a cage), a mesh bag, or the like, to be deployed within the intervertebral disc space or another appropriate anatomical location, respectively.

A workflow of performing a vertebral augmentation with the system 40 will now be described with particular reference to FIGS. 8-11, 13, 14 and 20. The vertebra with the offending vertebral body may be confirmed on fluoroscopic imaging. An incision may be made in the overlying paraspinal musculature lateral of midline generally in alignment with one of the pedicles of the vertebra. The distal end 52 of the access cannula 44, with the trocar disposed therein, is directed through the pedicle a position beyond the cortical rim and within the interior region of the vertebral body, and the trocar is removed. The access cannula 44 provides the working channel to within the interior region of the vertebral body along the longitudinal axis. The cannula hub 46 is exposed and configured to be engaged by the introducer device 42.

As previously mentioned, the shaft 110 of the introducer device 42 has a length sufficient to extend through and be operable beyond the distal end 52 of the access cannula 44. Further, the length of the shaft 110 is fixed relative to the actuator 54. Thus, when the introducer device 42 is positioned in operable engagement with the cannula hub 46 of the access cannula 44, the shaft 110 having a fixed length extends beyond the distal end 52 of the cannula shaft 48, also having a fixed length, by a fixed distance. In other words, with the access cannula 44 secured to the vertebra, the cannula hub 46 may be at a fixed distance from the distal end 52 and serve as a datum for subsequently introduced instrumentation. In certain instances, it may be desirable for the practitioner to have the shaft 110 of the introducer device 42 extend beyond the distal end 52 of the access cannula 44 by a distance less than the fixed distance. To do so, the practitioner may manually retract the introducer device 42 proximally relative to the access cannula 44. The arrangement may require the practitioner to manually support and control the introducer device 42, perhaps for prolonged periods, which may be undesirable or unfeasible with deploying additional instrumentation.

In some configurations, the system 40 of the present disclosure advantageously provides for the access cannula 44 being selectively adjustable such that the datum provided by the access cannula 44 may be selectively tuned. As a result, the practitioner may position the introducer device 42 in operable engagement with the cannula hub 46, as this is generally preferable, yet selectively control the distance of extension of the shaft 110 of the introducer device 42 from the distal end 52 of the access cannula 44. It is to be understood that the access cannula 44 that is adjustable is an optional feature of the system 40, and more conventional access cannulas may also be utilized.

Figure 8:
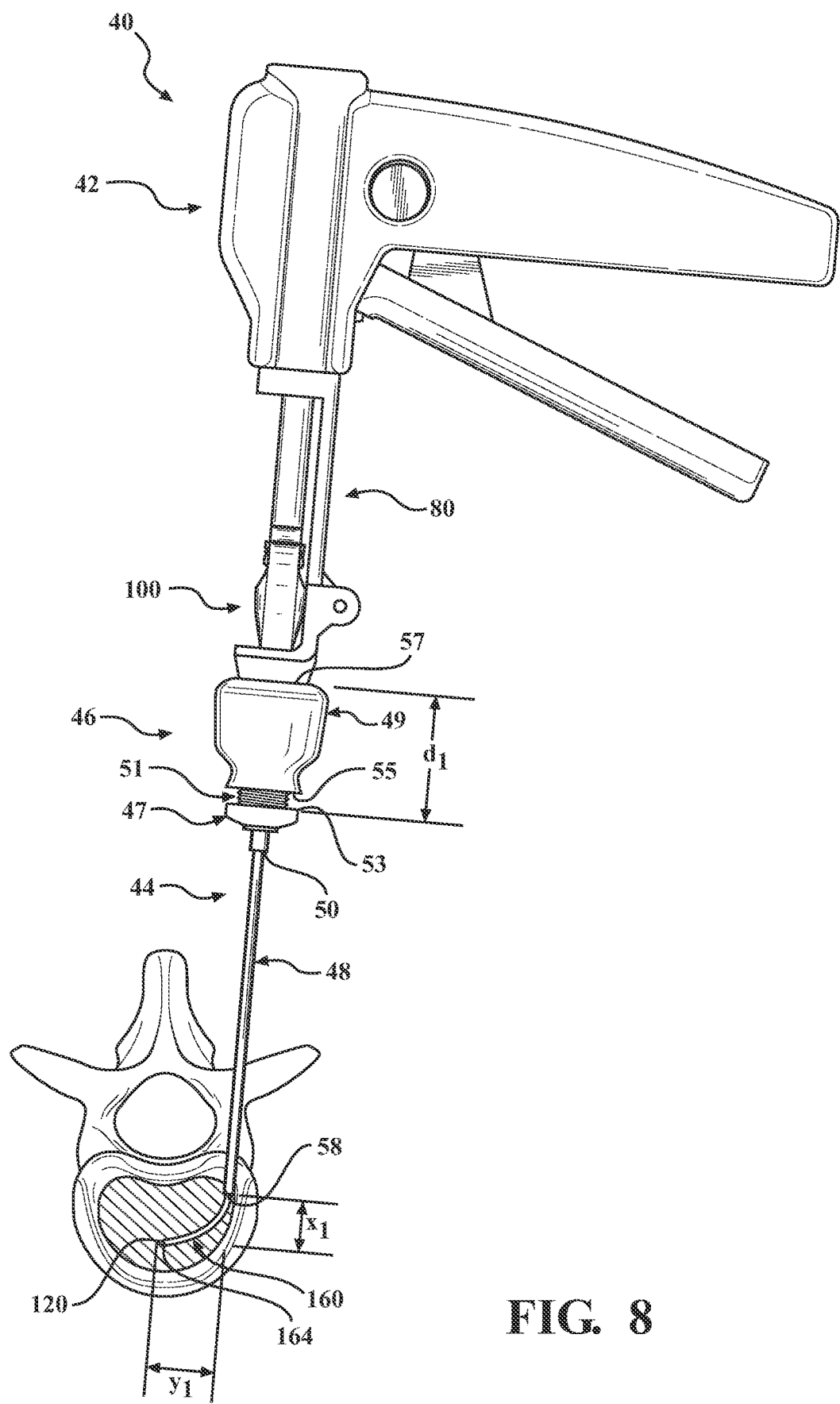
FIG. 8 shows the shaft and the flexible sheath of the introducer device extending through an access cannula adjustable to a first distance, and a distal end of the introducer device at a first position within the vertebral body based on the first distance of the adjustable access cannula.
Figure 9:
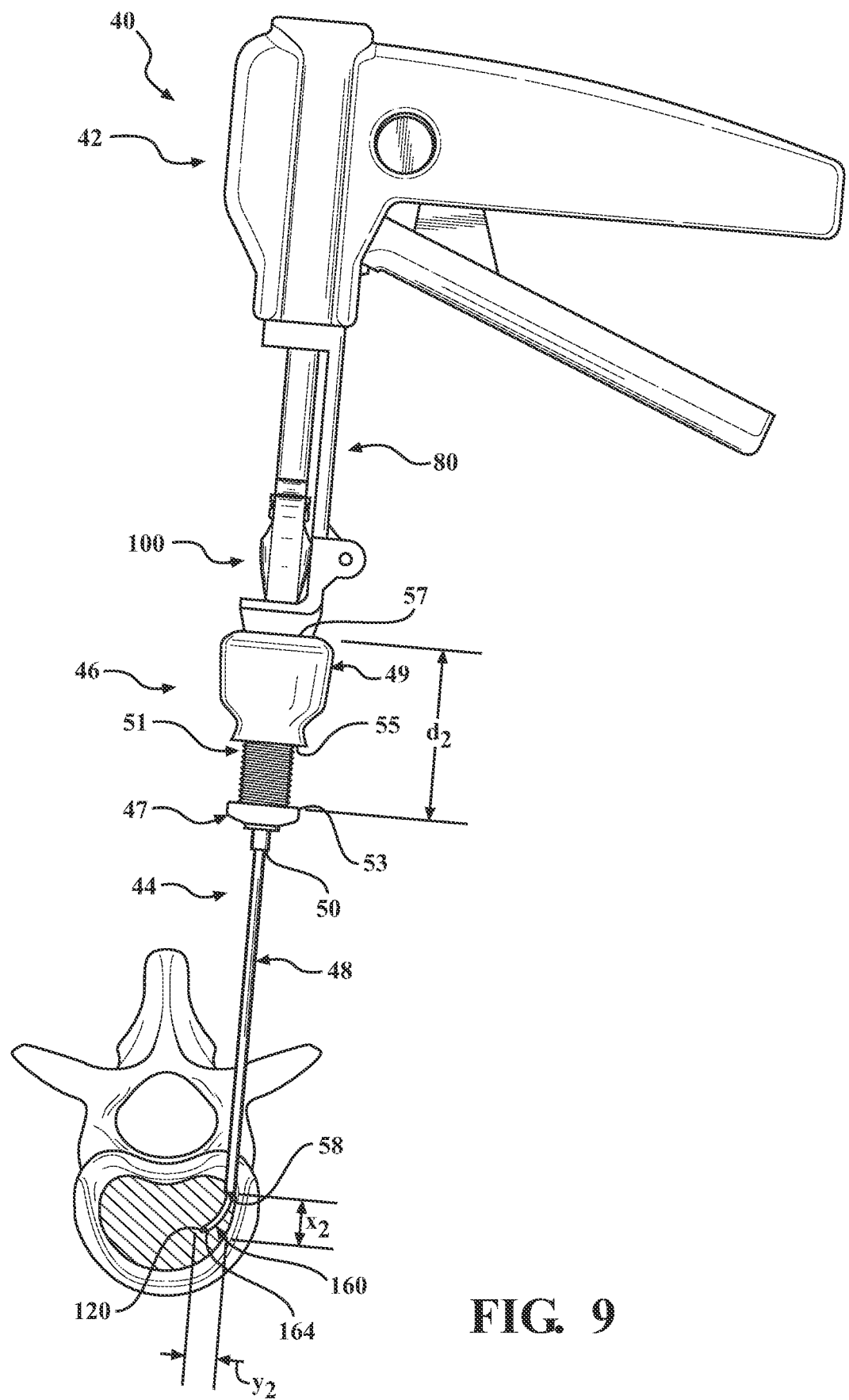
FIG. 9 shows the shaft and the flexible sheath of the introducer device extending through the access cannula adjustable to a second distance, and a distal end of the introducer device at a second position off-axis within the vertebral body based on the second distance of the adjustable access cannula.

Referring to FIGS. 8 and 9, the cannula hub 46 includes a shaft hub 47, a tuning hub 49, and complementary coupling features 51 movably coupling the tuning hub 49 to the shaft hub 47. The shaft hub 47 is rigidly coupled to the cannula shaft 48, and more particularly to the proximal end 50 of the cannula shaft 48. Each of the shaft hub 47 and the tuning hub 49 define bores (not identified) coaxially aligned with one another and with the lumen of the access cannula 44 for receiving an elongate member of instrumentation of the system 40, for example, the shaft 110 of the introducer device 42, the sheath 160 of the delivery cannula 100, and/or a balloon tube 204 of the expandable member assembly 200. The shaft hub 47 includes a proximally-directed surface 53, and owing to the cannula shaft 48 having a fixed length and being rigidly fixed to the cannula shaft 48, the proximally-directed surface 53 is at a fixed distance from the vertebral body when the distal end 52 of the cannula shaft 48 is positioned within the vertebral body. Thus, it may be considered that the proximally-directed surface 53 provides the datum previously mentioned. The tuning hub 49 is movably coupled to the shaft hub 47 with the coupling features 51. FIGS. 8 and 9 show the coupling features 51 including complementary threading. The tuning hub 49 may include a distally-directed surface 55, and an interference surface 57 opposite the distally-directed surface 55. The interference surface 57, in a broadest sense, is configured to be engaged by the instrumentation of the system 40, for example, the introducer device 42, the spacer hub 80, the delivery cannula 100, and/or the expandable member assembly 200. For example, FIGS. 8 and 9 show the distal portion 84 of the spacer hub 80 engaging the interference surface 57. The interference surface 57 prevents distal movement of the instrument 42, 80, 100, 200 relative to the access cannula 44 while permitting proximal movement of the instrument 42, 80, 100, 200 relative to the access cannula 44. In other words, a distance from the interference surface 57 to the proximally-directed surface 53 providing the datum contributes to the distance by which the shaft 110 of the introducer device 42 extends from the distal end 52 of the access cannula 44.

With continued reference to FIGS. 8 and 9, the tuning hub 49 is configured to be supported in a plurality of supported positions to facilitate selective adjustment of an axial position of the interference surface 57 of the tuning hub 49 relative to the datum. For example, the tuning hub 49 may be in an initial position (not shown) in which the distally-directed surface 55 of the tuning hub 49 abuts the proximally-directed surface 53 of the shaft hub 47. The interference surface 57 of the tuning hub 49 is at a minimum distance from the datum in the initial position. With the tuning hub 49 supported in the initial position, the shaft 110 of the introducer device 42 extends from the distal end 52 of the access cannula 44 by an initial length, which may be resolved in an x-component along the longitudinal axis and a y-component perpendicular to the longitudinal axis. With abutment of surfaces 53, 55 preventing further distal movement of the tuning hub 49 relative to the shaft hub 47, the initial distance may be a greatest length by which the shaft 110 of the introducer device 42 extends from the distal end 52 of the access cannula 44.

Prior to or after deploying the introducer device 42, the practitioner may selectively tune the access cannula 44 to selectively adjust the axial position of the interference surface 57 relative to the datum. The practitioner may proximally move the tuning hub 49 relative to the shaft hub 47 to a first position in which the interference surface 57 is at a first distance ($d_1$) from the datum provided by the shaft hub 47, as shown in FIG. 8. The selective adjustment of the interference surface 57 may be facilitated by the coupling features 51, for example the complementary threads, which move the tuning hub 49 relative to the shaft hub 47 upon receiving a twisting input from the practitioner.

With the introducer device 42 positioned in operable engagement with the cannula hub 46 (i.e., engaging the spacer hub 80 that is engaging the tuning hub 49), and with the tuning hub 49 supported in the first position, the shaft 110 of the introducer device 42 extends from the distal end 52 of the access cannula 44 by a first length. The first length may be resolved in the x-component ($x_1$) and the y-component ($y_1$). The practitioner may proximally move the tuning hub 49 relative to the shaft hub 47 to a first supported position in which the interference surface 57 is at a second distance ($d_2$) from the datum provided by the shaft hub 47, as shown in FIG. 9. With the instrument the introducer device 42 positioned in operable engagement with the cannula hub 46, and with the tuning hub 49 supported in the second supported position, the shaft 110 of the introducer device 42 extends from the distal end 52 of the access cannula 44 by a second length. The second length may be resolved in the x-component ($x_2$) and the y-component ($y_2$). It is appreciated that that second length is less than the first length in each of the x- and y-components, as the second distance is greater than the first distance, which increases an overall length of the access cannula 44 defined between the interference surface 57 and the distal end 52.

As mentioned, the instrument 42, 100, 200 may be the delivery cannula 100 including the delivery hub 102 and the sheath 160 extending from the delivery hub 102. FIGS. 8 and 9 show the delivery hub 102 abutting the distal portion 84 of the spacer hub 80, which is engaging the interference surface 57 of the tuning hub 49. The interference surface 57 may be selectively adjusted to move the distal end 164 of the sheath 160 relative to the distal end 52 of the access cannula 44. FIG. 8 shows the distal end 164 of the sheath 160 at the first length, resolved in the x- and y-components ($x_1$, $y_1$), with the interference surface 57 at the first distance ($d_1$) from the datum, and FIG. 9 shows the distal end 164 of the sheath 160 at the second length, resolved in the x- and y-components ($x_2$, $y_2$), with the interference surface 57 at the second distance ($d_2$) from the datum. Thus, with the tuning hub 49 in a desired one of the supported positions, the practitioner may enjoy the benefit of engaging the instrument 42, 100, 200 with the access cannula 44 (e.g., abutting, removably coupling, etc.), and achieving a desired length of extension of the instrument 42, 100, 200 from the distal end 52 of the access cannula 44 without needing to manually retract or support the instrument 42, 100, 200.

Figure 10:
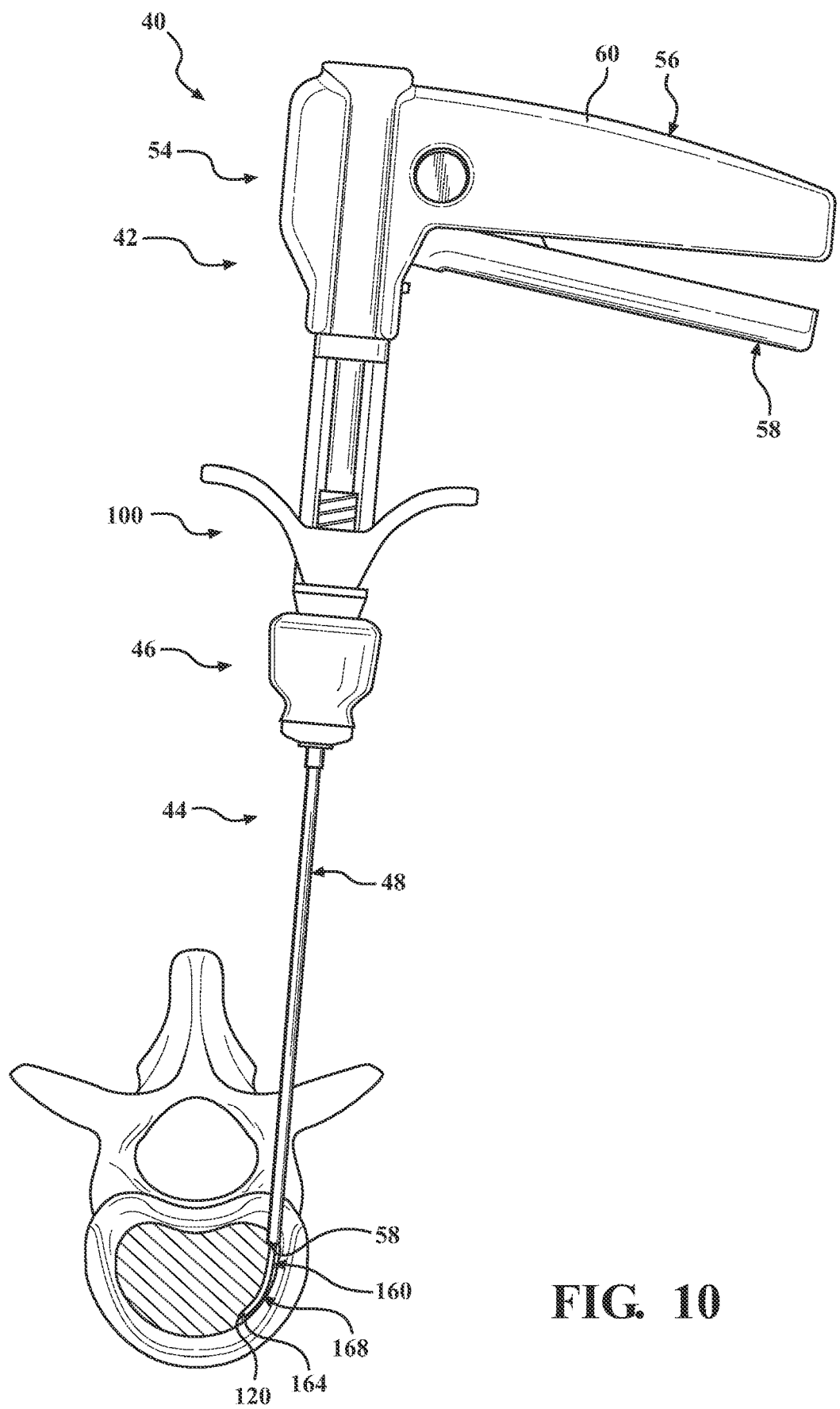
FIG. 10 shows the shaft and the flexible sheath of the introducer device extending through the access cannula with the actuator actuated and the pre-set curve of the shaft in the constrained state within the vertebral body.

Referring now to FIG. 10, the introducer device 42, including the sheath 160, is directed through the access cannula 44 in the manner previously described. In particular, the introducer device 42 may be provided with the pre-set curve in the unconstrained state, and the distal portion 168 of the sheath 160 conforming to the pre-set curve. The superelastic shape memory material biases the distal portion 114 of the shaft 110, along with the distal portion 168 of the sheath 160, away from an axis of the proximal portion 112 of the shaft 110. The practitioner provides an input to the actuator 54, for example moving the control surface 58 towards the handle 60, to increase the tension the pulling element 150. The tensioning of the pulling element 150 moves the pre-set curved from the unconstrained state to the constrained state against the biasing force from the superelastic shape memory material. In the constrained state, the pre-set curve at least partially straightens along with the distal portion 168 of the sheath 160. More particularly, the pre-set curve straightens to an extent that the distal portion 114 of the shaft 110 and the distal portion 168 of the sheath 160 may be directed through the lumen of the access cannula 44. It is understood that the distal portion 114 of the shaft 110 need not be entirely straight, as the access cannula 44 constrains the distal portion 114 as it is advanced therethrough. Yet the distal portion 114 of the shaft 110 should be straightened to an extent to permit ease with insertion of the shaft 110 and the sheath 160 along the lumen of the access cannula 44 as it is advanced therethrough. The pre-set curve may be selectively locked with the locking mechanism 59.

Figure 11:
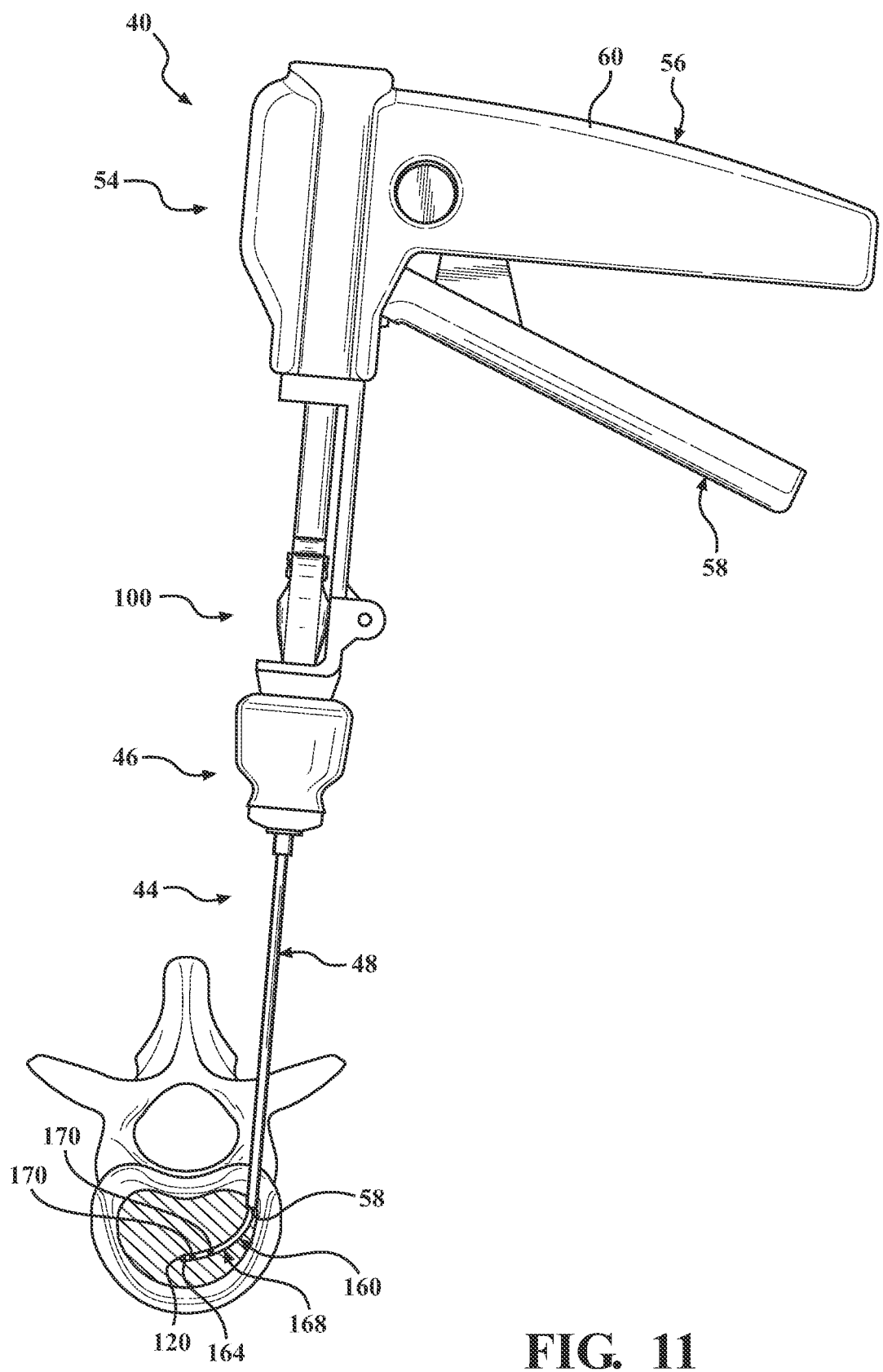
FIG. 11 shows the shaft and the flexible sheath of the introducer device extending through the access cannula with the pre-set curve of the shaft in the unconstrained state within the vertebral body.

The shaft 110 of the introducer device 42 and the sheath 160 of the delivery cannula 100 are directed through the access cannula 44 in the constrained state. Another input is provided to the actuator 54, which may be considered removal of the earlier input. The removal of the input may be performed quickly or in a controlled manner. The pulling element 150 is relaxed, and/or the tension on the pulling element 150 is reduced. The superelastic shape memory material releases the stored potential energy to move the pre-set curve from the constrained state to the unconstrained state. The removal of the input may be performed when the distal end 120 of the shaft 110 is at least substantially in registration with the distal end 52 of the access cannula 44. At least momentarily, the pre-set curve may not be constrained from the pulling element 150 but otherwise constrained from the cannula shaft 48 of the access cannula 44. The introducer device 42 and the sheath 160 are advanced distally relative to the access cannula 44 to position the distal portion 114 of the shaft 110 and the distal portion 168 of the sheath 160 within the interior of the vertebral body. As the introducer device 42 and the sheath 160 are being advanced, the pre-set curve, in the unconstrained state, displaces cancellous bone within the vertebral body, and/or positions the distal end 120 of the shaft 110 (as well as the distal end 164 of the sheath 160) at the target site that is offset from the longitudinal axis, as shown in FIG. 11. Additionally or alternatively, removal of the input may be performed while the distal portion 114 of the shaft 110 and the distal portion 168 of the sheath 160 are being advanced beyond the distal end 52 of the access cannula 44. The removal of the input while advancing may facilitate achieving a desired curvature (e.g., steeper or shallower) different than the curvature of the pre-set curve. The desired curvature may be facilitated by selectively locking the introducer device 42 with the locking mechanism 59 prior to advancement. Additionally or alternatively, removal of the input may be performed when the distal portion 114 of the shaft 110 and the distal portion 168 of the sheath 160 are positioned beyond the distal end 52 of the access cannula 44. The removal of the input after advancing may result in a sweeping motion within the vertebral body and displace cancellous bone accordingly, as generally shown in FIG. 1. The shaft 110 of the introducer device 42 may be removed from the sheath 160 with the sheath 160 remaining positioned at the target site offset from the longitudinal axis.

The system 40 advantageously facilitates repositioning of the sheath 160, and in particular without requiring the sheath 160 be removed from the access cannula 44 to be redeployed. Existing systems requiring removal of the sheath 160 may undesirably increase the likelihood of material degradation of the sheath 160. For example, in cases where a sheath is formed from a polymer such as PEEK, there may be pronounced frictional forces on the sheath 160 from the distal end 52 of the access cannula 44 as it is being removed. With the system 40 including the introducer device 42, the practitioner may provide another input to the actuator 54 to increase the tension the pulling element 150 while the distal portion 114 of the shaft 110 and the distal portion 168 of the sheath 160 are within the interior region of the vertebral body. The practitioner may manipulate the handle 60 as desired, then actuate the actuator to reduce the tension on the pulling element 150 to move the pre-set curve from the constrained state to the unconstrained state to position the distal portion 114 of the shaft 110 and the distal portion 168 of the sheath 160 at a second target site that is offset from the longitudinal axis. It is understood that any number of subsequent inputs may be provided to the control surface 58 to selectively adjust the curvature of the distal portion 114 of the shaft 110 and the distal portion 168 of the sheath 160, and multiple inputs may be provided for creating a cavity of a desired shape within the interior region of the vertebral body.

In certain implementations, it may be desirable to reposition the sheath 160 after removal of the introducer device 42 from the sheath 160, for example, after ascertaining positioning of the sheath 160 within the vertebral body as described below. The introducer device 42 may be directed through the sheath 160 in a manner similar to that previously described for the access cannula 44. In particular, the introducer device 42 may be actuated to approximate the curvature of the distal portion 168 of the sheath 160 as it is being directed therethrough. Once the introducer device 42 is deployed, the input(s) may be provided to and removed from the control surface 58 of the actuator 54 to reposition the sheath 160 at the second or subsequent target site without requiring removal of the sheath 160. The shaft 110 of the introducer device 42 may again be removed from the sheath 160 with the sheath 160 remaining positioned at the second or subsequent target site offset from the longitudinal axis.

Often, it is desirable to ascertain and/or confirm positioning of the instrumentation within the vertebral body. An existing manner by which this may be accomplished is a single radiopaque marking on a shaft detectable by fluoroscopy. The ascertaining and/or confirming positioning of the introducer device 42, given its selective adjustment of curvature, is associated with challenges not adequately addressed by existing devices. For example, a lateral x-ray image of the single radiopaque marking may not provide sufficient precision as to the extent of curvature in the mediolateral directions. Likewise, an anterior-posterior (A/P) image of the single radiopaque marking may not provide sufficient precision as to the position of the shaft in the anterior and posterior directions. Moreover, disposing the radiopaque marking(s) on the shaft does not adequately account for systems, such as the system 40 of the present disclosure, in which the shaft 110 is removed from within the sheath 160 and the sheath 160 remains movably positioned within the vertebral body. The shaft 110 may be formed from a polymer that is not meaningfully visible on x-ray imaging.

Figure 12:
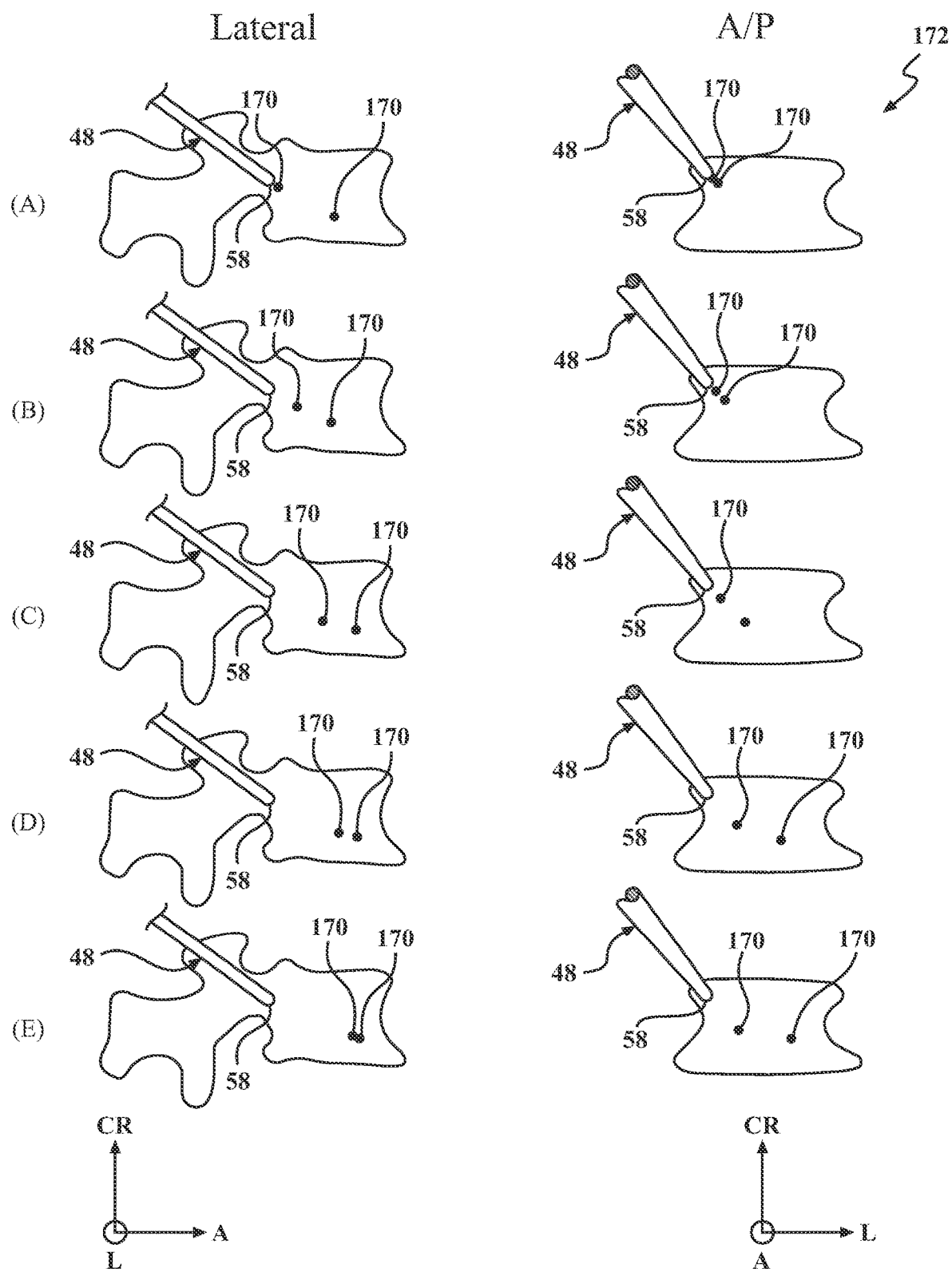
FIG. 12 is a schematic representation of five sets of lateral and anterior-posterior (A-P) x-ray images showing relative positions of the radiopaque markers of the flexible sheath in each of five configurations within the vertebral body.

The system 40 of the present disclosure advantageously provides features and methods for more accurately ascertaining and/or confirming intraoperatively, through fluoroscopic imaging, the position and/or the curvature of the distal portion 168 of the sheath 160 within the interior region of the vertebral body. The delivery cannula 100 of the system 40 includes at least two radiopaque markers 170 on the distal portion 168 of the sheath 160 (i.e., not on the shaft 110 of the introducer device 42) with the radiopaque markers 170 spaced apart from one another by a fixed spacing along the distal portion 168. The at least two radiopaque markers 170 may be exactly two radiopaque markers 170, however, three, four, or five or greater radiopaque markers may be used. The radiopaque markers 170 are detectable by fluoroscopy or other x-ray imaging device, and the x-ray images from the fluoroscopy are configured to be displayed on a display 172, referenced generally in FIG. 12. For example, the radiopaque markers 170 may be one of dots, bands, rings, and lines. FIG. 12 shows five sets of x-ray images with each set including a lateral x-ray image and a corresponding A/P x-ray image (labeled (A)-(E)). The cannula shaft 48 including its distal end 52 is shown positioned within a schematic representation of the vertebral body. The introducer device 42 is not shown in FIG. 12 (i.e., the shaft 110 has been removed from the sheath 160 or the shaft 110 is not meaningfully visible on fluoroscopy). It is to be understood that the radiopaque markers 170 are an optional feature of the system 40, and more conventional methods may also be utilized.

Referring first to Set A, the display 172 shows the lateral x-ray image in which the radiopaque markers 170 are spaced apart from one another at a first lateral distance in a first configuration, for example a first curved configuration. The display 172 shows the A/P x-ray image in which the radiopaque markers 170 are spaced apart from one another at a first A/P distance in the first configuration. The first lateral distance is greater than the first A/P distance, and Set A may be representative of at least one of (a) the pre-set curve of the shaft 110 being in the constrained state, and (b) the distal portion 168 of the sheath 160 being just beyond the distal end 52 of the access cannula 44. The latter includes the sheath 160 is exposed minimally from the access cannula 44, and thus the sheath 160 is unable to curve more than minimally. Given the posterior approach of the access cannula 44, the radiopaque markers 170 appear adjacent one another in the first A/P image. In the first lateral x-ray image, however, the relatively minimal curvature results in the radiopaque markers 170 appearing at or nearly at the fixed spacing along the distal portion 168, because the pre-set curve of the shaft 110 is substantially straight.

Set B shows a second configuration, for example a second curved configuration, which may be representative of at least one of (a) the pre-set curve of the shaft 110 being in a slightly less constrained state than the first configuration shown in Set A, and (b) the distal portion 168 of the sheath 160 being positioned beyond the position of the distal portion 168 shown in Set A. The display 172 shows the lateral x-ray image in which the radiopaque markers 170 are spaced apart from one another at a second lateral distance in the second configuration, and the A/P x-ray image in which the radiopaque markers 170 are spaced apart from one another at a second A/P distance in the second configuration. The second lateral and A/P distances are different than the first lateral and A/P distances. Further, the second lateral distance is less than the first lateral distance, and the second A/P distance is greater than the first A/P distance. In other words, as the sheath 160 is curved into the paper of the left column of lateral x-ray images of FIG. 13, the distance between the two radiopaque markers 170 will appear to decrease. Likewise, the corresponding curving of the sheath 160 of the right column of A/P x-ray images is to the right, and the distance between the two radiopaque markers 170 will appear to increase.

Set C shows a third configuration, for example a third curved configuration, which may be representative of at least one of (a) the pre-set curve of the shaft 110 being in a slightly less constrained state than the second configuration shown in Set B, and (b) the distal portion 168 of the sheath 160 being positioned beyond the position of the distal portion 168 shown in Set B. The display 172 shows the lateral x-ray image in which the radiopaque markers 170 are spaced apart from one another at a third lateral distance in the third configuration, and the A/P x-ray image in which the radiopaque markers 170 are spaced apart from one another at a third A/P distance in the third configuration. The third lateral distance is less than the second lateral distance, and the third A/P distance is greater than the second A/P distance. Set D shows a fourth configuration, for example a fourth curved configuration, which may be representative of at least one of (a) the pre-set curve of the shaft 110 being in a slightly less constrained state than the third configuration shown in Set C, and (b) the distal portion 168 of the sheath 160 being positioned beyond the position of the distal portion 168 shown in Set C. The display 172 shows the lateral x-ray image in which the radiopaque markers 170 are spaced apart from one another at a fourth lateral distance in the fourth configuration, and the A/P x-ray image in which the radiopaque markers 170 are spaced apart from one another at a fourth A/P distance in the fourth configuration. The fourth lateral distance is less than the third lateral distance, and the fourth A/P distance is greater than the third A/P distance. Finally, Set E shows a fifth configuration, for example a fifth curved configuration, which may be representative of at least one of (a) the pre-set curve of the shaft 110 being in the unconstrained state, and (b) the distal portion 168 of the sheath 160 being fully extended from the access cannula 44. The display 172 shows the lateral x-ray image in which the radiopaque markers 170 are spaced apart from one another at a fifth lateral distance in the fifth configuration, and the A/P x-ray image in which the radiopaque markers 170 are spaced apart from one another at a fifth A/P distance in the fifth configuration. The fifth lateral distance is less than the fourth lateral distance, and the fifth A/P distance is greater than the fourth A/P distance.

With the at least two radiopaque markers 170 on the sheath 160, relative positions between the radiopaque markers 170 may be viewable on the x-ray imaging to determine a curvature of the distal portion 168 of the sheath 160. Further, utilizing the lateral and A/P x-ray imaging in tandem in the aforementioned manner facilitates visually ascertaining and/or confirming intraoperatively the position and/or the curvature of the distal portion 168 of the sheath 160 within the interior region of the vertebral body, particularly in three-dimensions. The lateral x-ray images provide the practitioner with precise positional information in the cranial (CR) and anterior (A) directions, and additional deducible information in the lateral (L) direction (i.e., based on practitioner experience assessing the relative positions between the radiopaque markers 170). The A/P x-ray images provide the practitioner with precise positional information in the cranial (CR) and lateral (L) directions, and additional deducible information in the anterior (A) direction. Collectively, the practitioner is able to view the x-ray image set on the display 172 and readily ascertain the position and/or curvature of the distal portion 168 of the sheath 160 within the interior region of the vertebral body. Still further, with the shaft 110 of the introducer device 42 removed from the sheath 160, the sheath 160 may be moved as desired with the ability to quickly confirm an updated position and/or curvature of the distal portion 168 of the sheath 160. It is contemplated that the at least two radiopaque markers 170 on the sheath 160 may utilized with the system disclosed in the aforementioned U.S. Pat. No. 8,894,658.

Figure 13:
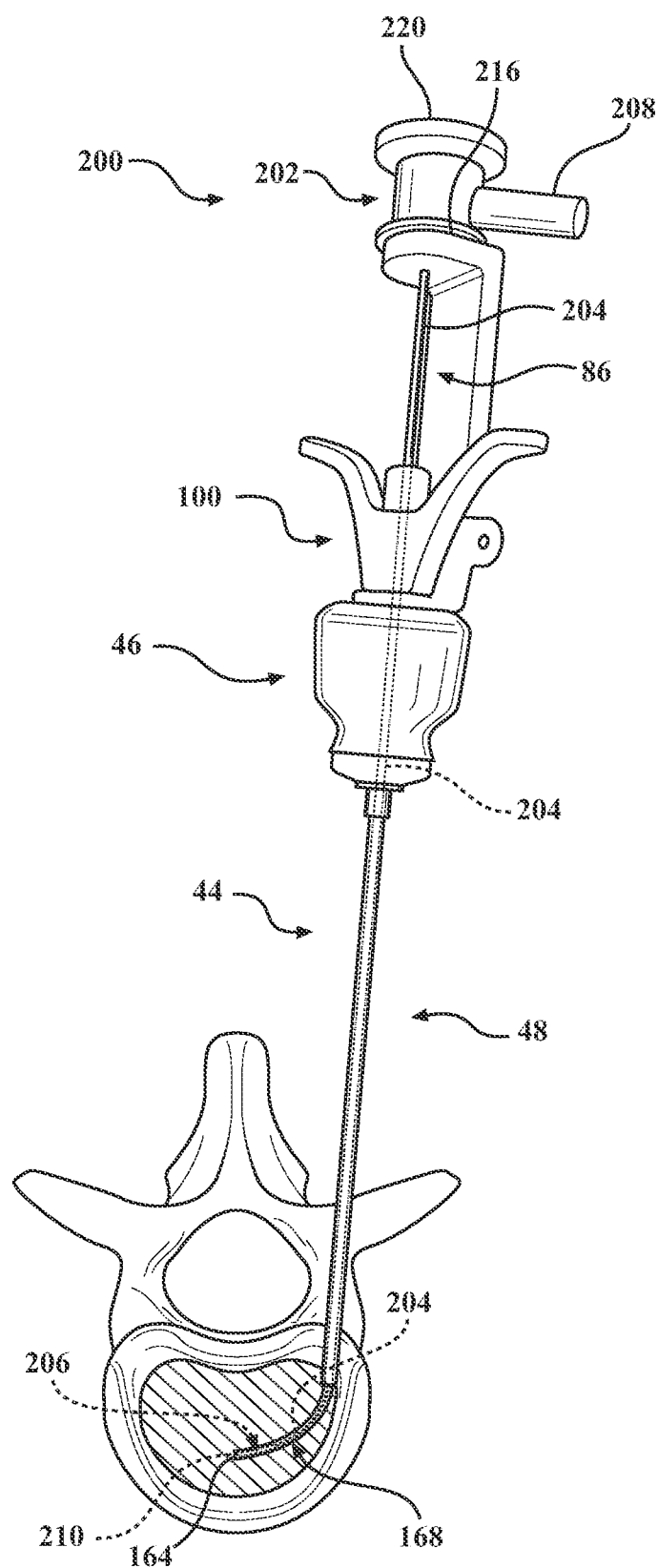
FIG. 13 shows a flexible distal portion of the flexible sheath in a curved configuration with an expandable member assembly including a balloon removably positioned within the flexible distal portion. A spacer hub engaging the access cannula is in a first position, and a delivery hub coupled to the flexible sheath is spaced apart from a balloon hub of the expandable member assembly.
Figure 14:
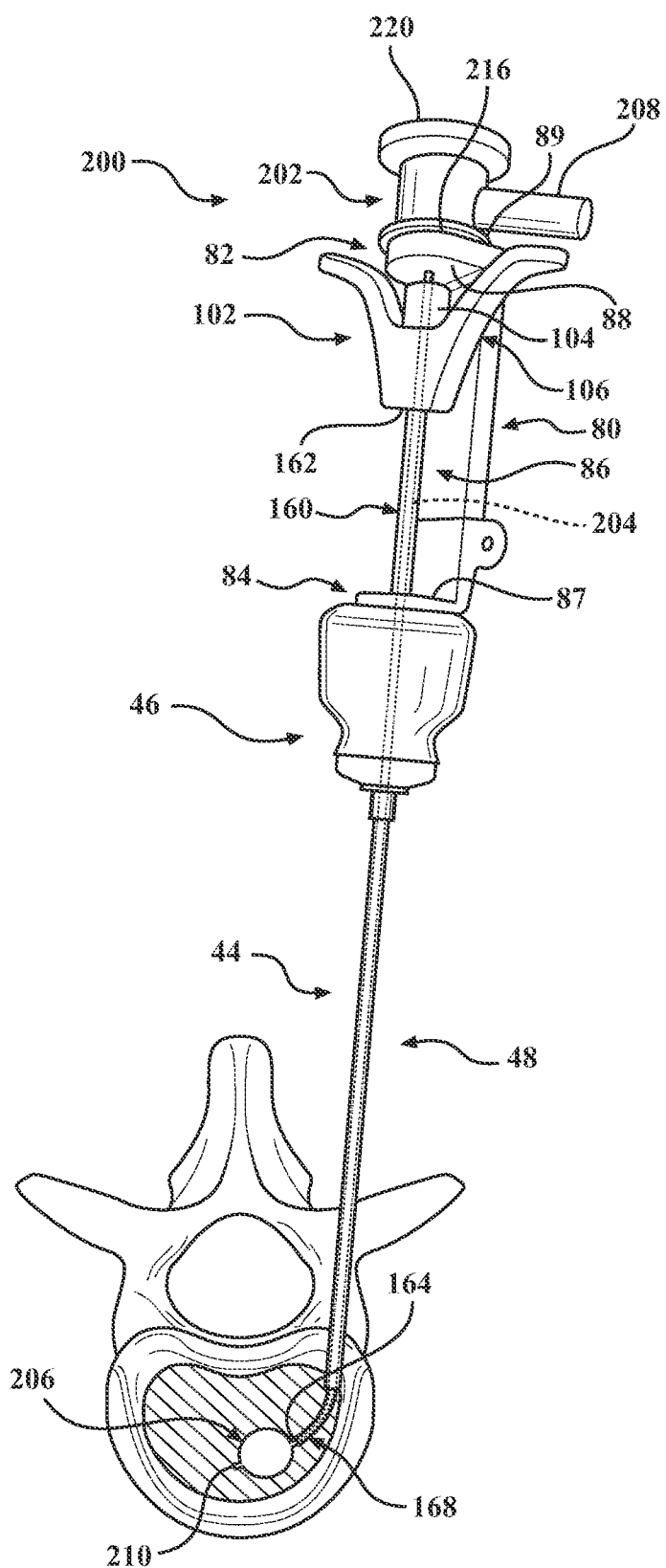
FIG. 14 shows the flexible distal portion of the flexible sheath in the curved configuration. The spacer hub engaging the access cannula is in the first position. The delivery hub is moved towards the balloon hub to retract the flexible sheath and expose the balloon within the vertebral body.
Figure 15:
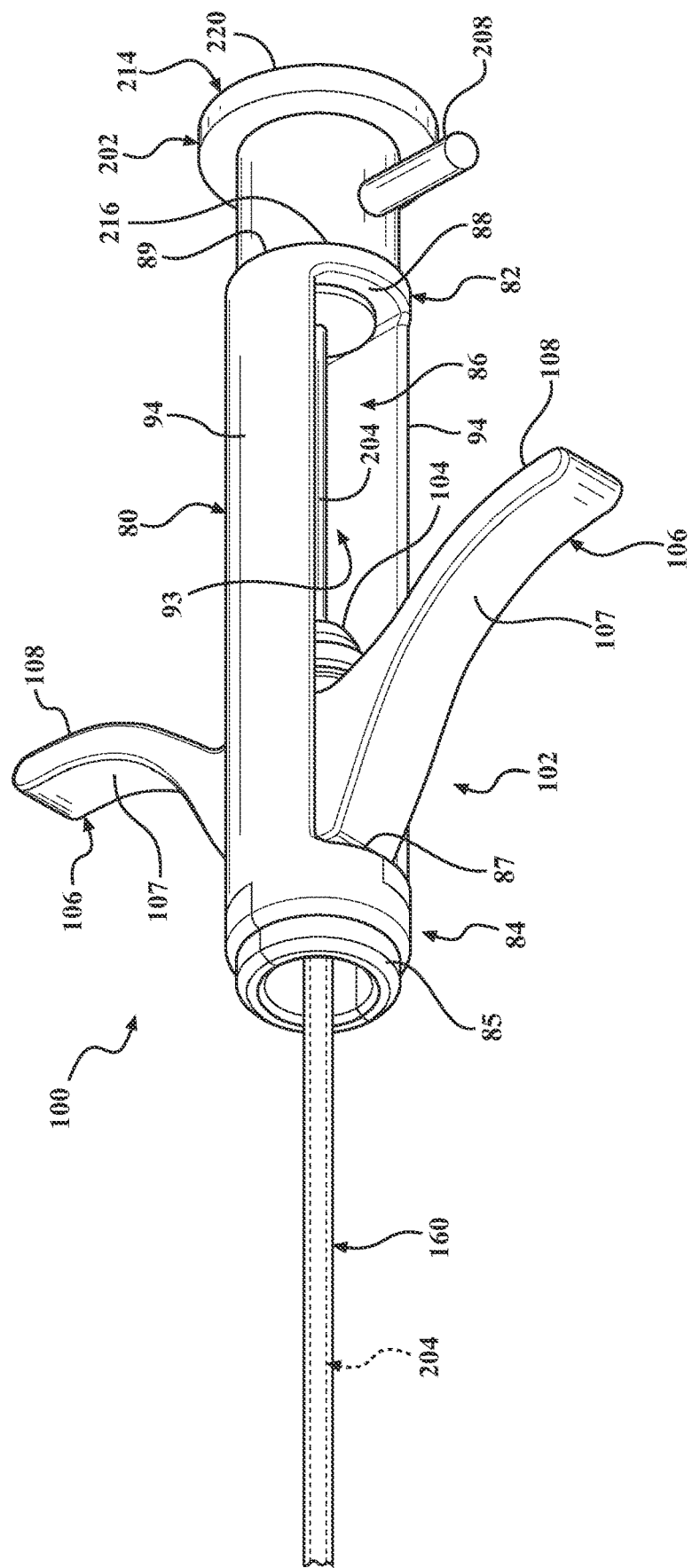
FIG. 15 is a detailed perspective view of the balloon hub and the delivery hub operably coupled to a spacer hub.

With the introducer device 42 removed from the delivery cannula 100 with the distal end 164 of the sheath 160 remaining positioned at the target site offset from the longitudinal axis, the expandable member assembly 200 may be deployed. Referring to FIGS. 13-15, the expandable member assembly includes a balloon hub 202, the balloon tube 204, and a balloon 206. The balloon tube 204 extends from the balloon hub 202, and the balloon 206 is disposed at a distal end of the balloon tube 204. The balloon hub 202 includes a fitting 208 adapted to be coupled with a fluid line in communication with a source of incompressible fluid (not shown), for example, air. The balloon 206 is configured to receive fluid from the source of fluid through the balloon hub 202 and the balloon tube 204 to be moved between a deflated state and an inflated state having a volume greater than the deflated state. In the deflated state, the balloon 206 and the balloon tube 204 are sized to be slidably inserted or directed through the lumen 166 of the sheath 160. The balloon tube 204 may include a length sufficient for the balloon 206 to extend beyond the distal end 164 of the sheath 160 and within the interior region of the vertebral body. The balloon 206 is moved to the inflated state to compress or otherwise displace cancellous bone within the vertebral body at the target site. Returning the balloon 206 to the deflated state may result in a cavity being formed within the cancellous bone for delivery of the curable material (see FIG. 20).

The balloon tube 204 and/or the balloon 206 are sufficiently flexible to follow the pathway defined by the lumen 166 of the sheath 160, including the distal portion 168 in the curved configuration. In other words, directing the balloon 206 through the sheath 160 should not alter the curvature of the distal portion 168 of the sheath 160. Owing to the flexibility of the balloon tube 204 and/or the balloon 206, the expandable member assembly 200 may lack sufficient columnar strength to be advanced beyond the distal end 164 of the sheath 160 to penetrate the cancellous bone of the interior region. Additionally or alternatively, urging the expandable member assembly 200 to penetrate the cancellous bone may result in the trabeculae of the cancellous bone causing the balloon 206 to deviate from the desired path previously created by the introducer device 42 and/or the target site previously accessed by the introducer device 42. The system 40 of the present disclosure advantageously provides for moving the sheath 160 relative to the expandable member assembly 200 to unsheathe and sheathe the balloon 206. Moreover, the unsheathing and sheathing the balloon 206 may be performed with a syringe-style input to be further explained that is both intuitive to the practitioner and provides the practitioner with improved feel.

The spacer hub 80 previously introduced, in cooperation with the balloon hub 204, facilitates the syringe-style input. Referring to FIGS. 1-3, 8-11 and 13-20, the spacer hub 80, in a broadest sense, is configured to facilitate proximal and distal movement of the delivery cannula 100 relative to the access cannula 44 while maintaining a position of the expandable member assembly 200 relative to the access cannula 44. The result includes proximal and distal movement of the delivery cannula 100 including the sheath 160 relative to the expandable member assembly 200 including the balloon 206, hence unsheathing and sheathing the balloon 206, respectively. It is to be understood that the spacer hub 80 is an optional feature of the system 40, and more conventional methods may also be utilized.

Figure 16:
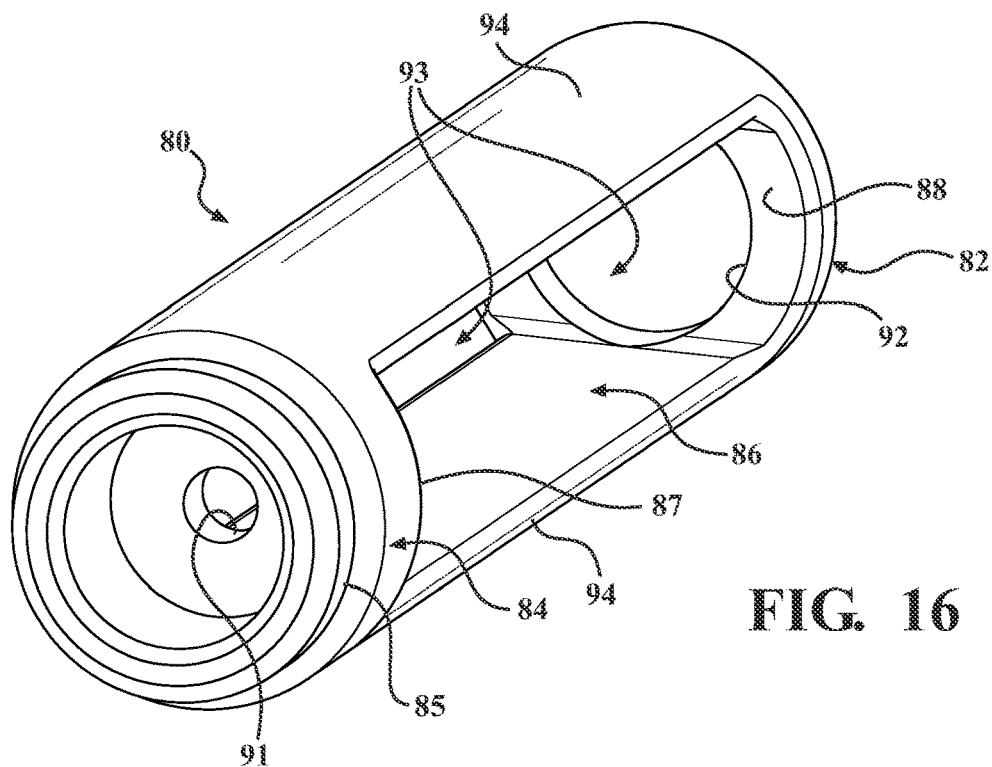
FIG. 16 is a perspective view of the spacer hub of FIG. 15.
Figure 17:
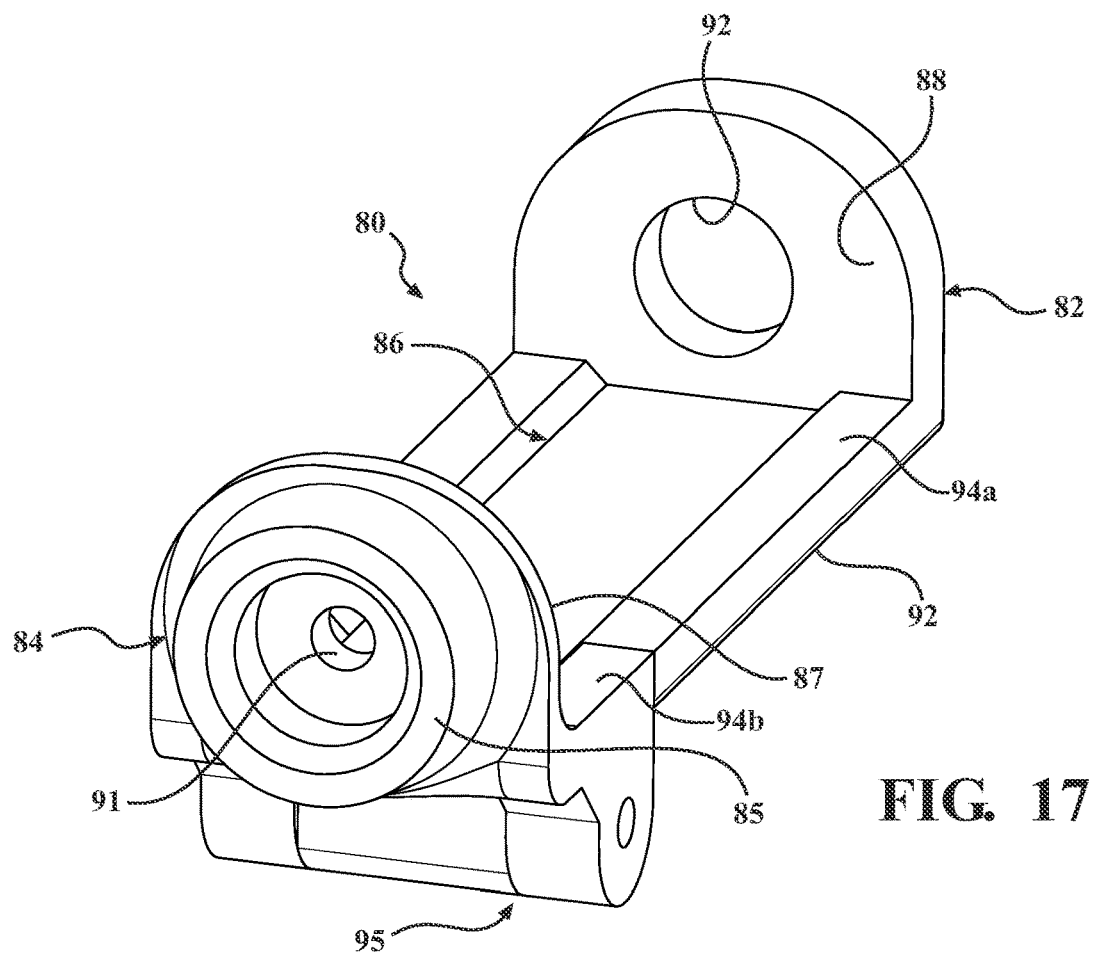
FIG. 17 is a perspective view of the spacer hub of FIGS. 13 and 14.

The spacer hub 80 includes a distal portion 84 configured to engage the cannula hub 46, and more particularly the tuning hub 49, as shown in FIG. 1. The distal portion 84 may include a boss 85 sized to be seated within a complementary cavity in the cannula hub 46 (see FIGS. 18 and 19). Each of the distal portion 84 and the cannula hub 46 may include complementary coupling features (not shown), for example a releasable detent, configured to removably couple the spacer hub 80 to the access cannula 44. The spacer hub 80 further includes the proximal portion 82 configured to be engaged by the balloon hub 202, as best shown in FIGS. 13-15. The proximal and distal portions 82, 84 are spaced apart from one another to define a void space 86 within which the delivery hub 102 of the delivery cannula 100 is configured to be movably disposed. The spacer hub of FIG. 16 shows the proximal and distal portions 82, 84 as ring-like structures, and the spacer hub 80 of FIG. 17 show the proximal and distal portions 82, 84 as flange-like structures.

Each of the proximal and distal portions 82, 84 include a stop surface 87, 88 defining the void space 86 with the stop surfaces 87, 88 providing a terminus of movement of the delivery hub 102 in a manner to be explained. The delivery hub 102 abuts or engages the stop surface 87 of the distal portion 84 in a first position, and the balloon hub 202 engages a surface 89 of the proximal portion 82 opposite the stop surface 88. The resulting arrangement is shown in FIGS. 13 and 15. The proximal and distal portions 82, 84 may each define an aperture 90, 91 coaxially aligned with one another and with a bore extending through the cannula hub 46 that is further aligned and in communication with the lumen of the cannula shaft 48. The aperture or opening 90 on the distal portion 84 is at least sized to receive the balloon tube 204, and the aperture 91 or opening of the proximal portion 82 is at least sized to receive a nose 212 of the balloon hub 202 (see FIGS. 21 and 22) to facilitate engagement of the balloon hub 202 with the spacer hub 80. The aperture 91 may also be at least sized to receive the barrel 68 of the actuator 54 with the barrel 68 extending through the proximal portion 82, as previously mentioned. As it is now understood that the delivery hub 102 may move proximally within the void space 86, the barrel 68 of the actuator 54 extends through the aperture 91 to within the void space 86 and into abutment with the delivery hub 102 to prevent premature proximal movement of the delivery cannula 100 while the introducer device 42 is being placed within the vertebral body through the access cannula 44 (see FIGS. 1-3). In other words, friction between the cancellous bone and the distally-advancing sheath 160 may result in proximal forces on the delivery cannula 100, and the barrel 68 of the actuator 54 abutting the delivery hub 102 maintains the delivery cannula 100 in a static position until the introducer device 42 is removed from the delivery cannula 100.

With the balloon hub 202 engaging the spacer hub 80 and the delivery hub 102 in the first position, the balloon tube 204 may extend through, in sequence, the aperture 92 of the proximal portion 82, the void space 86, the aperture 91 of the distal portion 84, a bore of the delivery hub 102, and the sheath 160 extending through the bore of the cannula hub 46 and the lumen of the cannula shaft 48. With the delivery hub 102 in the first position, a distal end 210 of the balloon 206 is near or in registration with the distal end 164 of the sheath 160, as shown in FIG. 13. The balloon 206 is in the deflated state and sheathed within the distal portion 168 of the sheath 160 in the curved configuration.

The balloon 206 may be unsheathed by moving the delivery cannula 100 proximally, and more particularly providing an input to move the delivery hub 102 proximally within the void space 86 of the spacer hub 80. The delivery hub 102 includes wings 106 extending laterally and defining first control surfaces 107 for receiving the input from the practitioner. FIG. 15 best shows the wings 106 being arcuate in shape and mirrored relative to one another with each of the wings 106 configured to ergonomically be engaged by one or more fingers of the practitioner. In one example, one of the wings 106 is engaged by the index finger of the practitioner, and the other one of the wings 106 is engaged by the middle finger of the practitioner. In at least some respects the ergonomics are similar to the flanges of a barrel of a medical syringe. The practitioner provides the input to the first control surfaces 107, and the delivery hub 102 moves proximally within the void space 86, for example into engagement with the stop surface 89 of the proximal portion 82 of the spacer hub 80, as shown in FIG. 14. The delivery hub 102 may be moved a desired distance, and/or a set distance until contacting the stop surface 89. The set distance may correspond to at least the distance required to unsheathe the balloon 206 based on its length. With continued reference to FIG. 14, the proximal movement of the delivery hub 102 results in proximal movement of the sheath 160 coupled to the delivery hub 102 with such movement being relative to the expandable member assembly 200 remaining in a static position. The balloon 206 is unsheathed and exposed within the interior region of the vertebral body in the deflated state, after which the balloon 206 may be moved to the inflated state to displace the cancellous bone.

Figure 21:
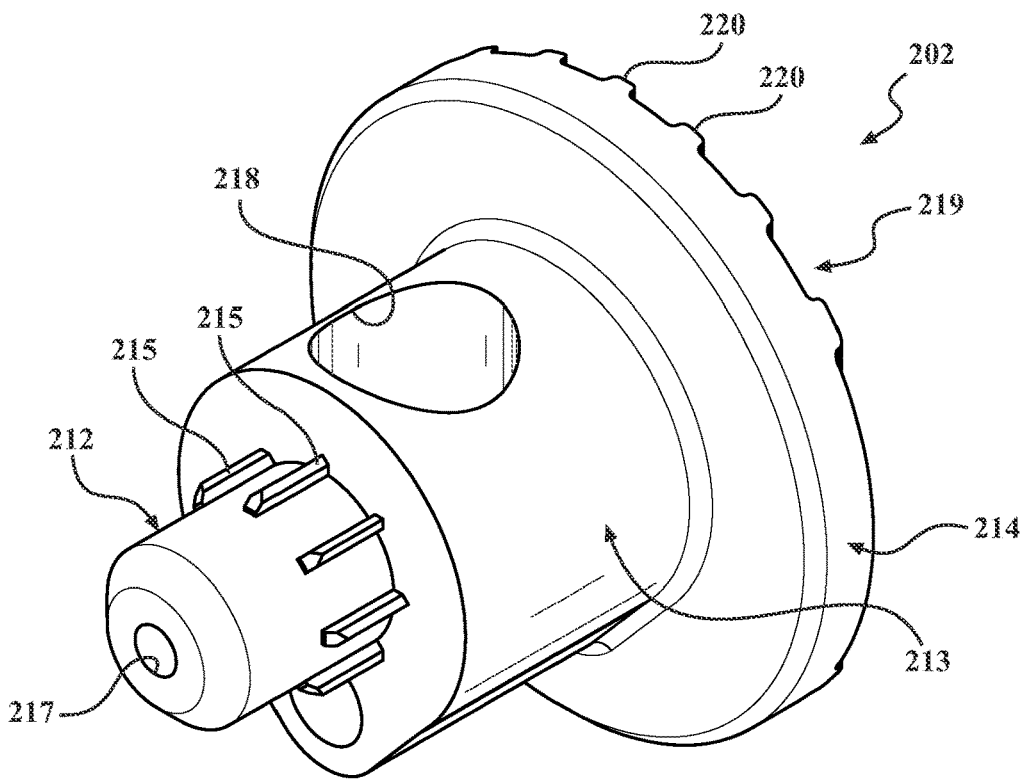
FIG. 21 is a front perspective view of the balloon hub of the expandable member assembly.
Figure 22:
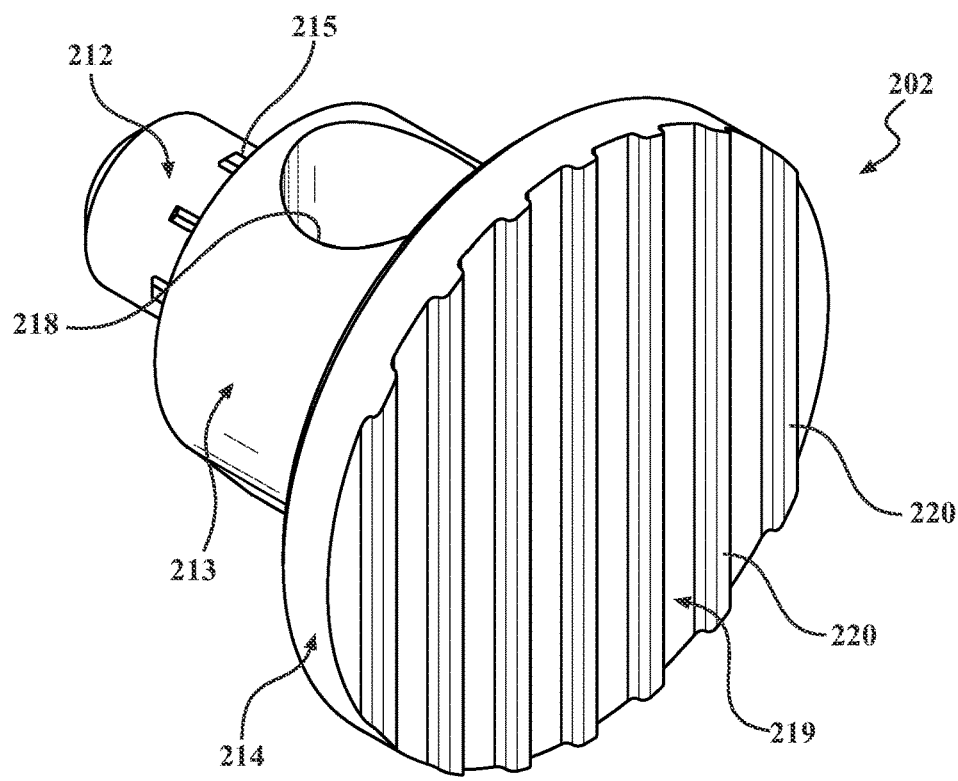
FIG. 22 is a rear perspective view of the balloon hub of the expandable member assembly.

The expandable member assembly 200 may remain in the static position through a complementary input to the balloon hub 202 as the input is provided to the first control surfaces 107. FIGS. 21 and 22 show the balloon hub 202 including a body portion 213, the nose 212 extending distally from the body portion 213, and a flange portion 214 extending proximally from the body portion 213. The nose 212 may be cylindrical in shape and sized to be positioned within the aperture 91 of the proximal portion 82 of the spacer hub 80. One or more rails 215 may extend radially from the nose 212 to further facilitate the engagement of the balloon hub 202 with the spacer hub 80. The body portion 213 may be relatively cylindrical in shape with an outer dimension greater than the outer diameter of the nose 212. A transition surface 216 may demarcate the transition from the nose 212 to the body portion 213. The transition surface 216 may contact the stop surface 89 when the balloon hub 202 engages the spacer hub 80, for example, as shown in FIGS. 14 and 15. The flange portion 214 may be cylindrical in shape with an outer dimension greater than the outer diameter of the body portion 213. A lumen 217 extends through the nose 212 and the body portion 213 and is in communication with a borehole 218 extending radially from the body portion 213. The borehole 218 is configured to be coupled with the fitting 208 (see FIG. 13), which is adapted to be in placed in communication with the fluid line.

A proximal side of the flanged portion 214 may define a control surface 220 configured to receive an input from the practitioner, also referred to as a second control surface. The flanged portion 214 may be circular in shape and include gripping features 219, for example the ridges shown in FIG. 22. With the borehole 218 positioned distal to the flanged portion 214 and further extending from the body portion 213 oriented transverse to the lumen 217 extending through the nose 212 and the body portion 213, an entirety of the control surface 220 is unobstructed, exposed, or otherwise available to the practitioner for the practitioner to provide the syringe-style input. In other words, the control surface 220 may be the proximal-most surface of the system 40 and sized to be engaged by a thumb of the practitioner.

The practitioner provides the input to the first control surfaces 107 while simultaneously providing an input to the second control surface 220. More particularly, the syringe-style input may include one of the first control surfaces 107 is engaged by the index finger of the practitioner, the other one of the first control surfaces 107 being engaged by the middle finger of the practitioner, and the second control surface 220 being engaged by the thumb of the practitioner. The arrangement and ergonomics may be similar to the medical syringe, and thus the arrangement is intuitive to the practitioner. The syringe-style input may include the thumb maintaining the position of the expandable member assembly 200 while at least one finger actuates first the control surface 107 to draw the delivery hub 102 towards the balloon hub 202.

Figure 20:
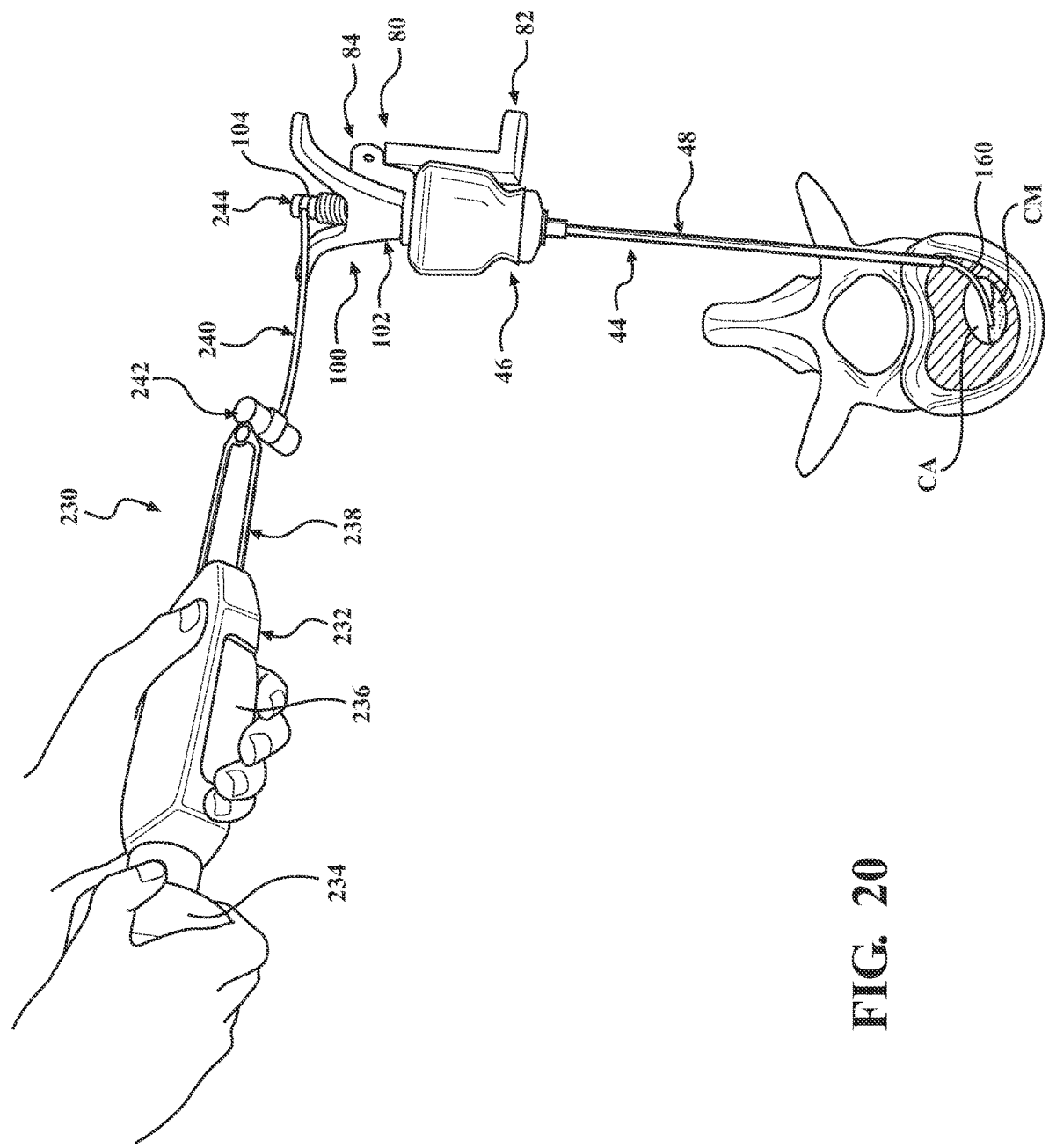
FIG. 20 shows the spacer hub in the second position, and a cement delivery system operably coupled to the delivery hub of the delivery cannula delivers bone cement within the vertebral body.

With the balloon 206 in the inflated state, the balloon 206 is returned to the deflated state to form the cavity within the cancellous bone for delivery of the curable material (see FIG. 20). Moving the balloon 206 into and through the sheath 160 may be associated with undesirable interference at the distal end 164 of the sheath 160. The retraction of the balloon 206 into the aperture at the distal end 164 may result in component compromise and/or the forces on the distal end 164 of the sheath 160 may cause the sheath 160 deviate from its existing path or curvature. The subsequent delivery of the curable material may not be properly located with the formed cavity. As a result, the present system 40 advantageously provides for sheathing the balloon 206 prior to withdrawal. The wings 106 define second control surfaces 108 generally opposite the first control surfaces 107. The second control surfaces 108 are configured to receive another input from the practitioner. The practitioner provides the input to the second control surfaces 108, and the delivery hub 102 moves distally within the void space 86, for example into engagement with the stop surface 88 of the distal portion 84 of the spacer hub 80, as shown in FIGS. 14 and 16. The delivery hub 102 moves the set distance corresponding to at least the distance required to sheathe the balloon 206 based on its length. Any resistance may be felt by the practitioner, which can be gradually addressed through further deflation of the balloon 206 and urging of the delivery hub 102 distally. The distal movement of the delivery hub 102 results in distal movement of the sheath 160 coupled to the delivery hub 102 with such movement being relative to the expandable member assembly 200 remaining in a static position. The balloon 206 is sheathed within the distal portion 168 of the sheath 160, after which it can be confidently removed from the access cannula 44 and the delivery cannula 100, for example, through a pulling input to the balloon hub 204.

As the delivery hub 102 moves between the first and second positions, the delivery hub 102 may be radially constrained by the balloon tube 204 extending from the balloon hub 202. In other words, the delivery hub 102 may "ride" on the balloon tube 204. Further, the spacer hub 80 of FIGS. 15 and 17 may rotationally constrain the delivery hub 102. The spacer hub 80 of FIGS. 15 and 17 includes opposing sides 94 defining opposed slots 93 between the opposing sides 94. The slots 93 are sized to receive the wings 106 of the cannula hub 46, as best shown in FIG. 15. Constraining the delivery hub 102 from rotation prevents the sheath 160 from correspondingly rotating within the vertebral body, which may prevent kinking of the sheath 160 and/or prevent the sheath 160 from deviating from its existing path or curvature. Further, the wings 106 remaining in a fixed rotational position may instill confidence to the practitioner that the curvature of the distal portion 168 of the sheath 160 is correspondingly fixed.

The spacer hub 80 may be configured to pivot for exposing the coupler 104 of the delivery hub 102 for coupling of a cement delivery system 230 to be described. Referring to FIGS. 13, 14 and 17-20, the spacer hub 80 may include a pivot 95 pivotably coupling the distal portion 84 to the proximal portion 82. Each of the proximal and distal portions 82, 84 may include a surface 94a, 94b collectively forming the side 94 of the spacer hub 80. The pivot 95 couples the surfaces 94a, 94b such that, when the spacer hub 80 is provided between a first position shown in FIG. 17 and a second position shown in FIG. 19, the proximal portion 82 articulates in a direction away from the void space 86. In other words, in certain configurations, the spacer hub 80 may be generally U-shaped when in the first position with the surfaces 94a, 94b generally aligned, for example coplanar. In the second position, the proximal portion 82 may substantially inverted and the surfaces 94a, 94b are parallel.

Moving the spacer hub 80 from the first position to the second position may provide better access to the delivery hub 102, and more particularly the coupler 104, for coupling of the cement delivery system 230. FIGS. 18 and 19 show the delivery hub 102 in phantom and positioned in the first position in engagement with the distal portion 84 of the spacer hub 80. While a portion of the void space 86 above the delivery hub 102 may provide some lateral access to the coupler 104, it may be desirable to move the spacer hub 80 from the first position to the second position in the manner previously described to render the coupler 104 of the delivery hub 102 the proximal-most component of the system 40.

Referring now to FIG. 20, the cement delivery system 230 may include a housing 232, a first control surface 234 coupled to the housing, and a second control surface 236 coupled to the housing 232. The first and second control surfaces 234, 236 are configured to receive inputs from the practitioner. For example, a rotational input to the first control surface 234 with one hand of the practitioner may advance a piston (not shown) with a chamber 238 to urge the curable material through the system 230. An input to the second control surface 236 with the other hand of the practitioner may be required to permit advancement of the piston, and release of the input to the second control surface 236 may act as a "dead man's switch" for ceasing distal movement of the piston (and permitting proximal movement of the piston). Operation of the cement delivery system 230 is further disclosed in commonly owned U.S. Patent Application No. 62/656,033, filed Apr. 11, 2018, the entire contents of which are hereby incorporated by reference. Another suitable cement delivery system is disclosed in commonly owned U.S. Pat. No. 6,547,432, issued Apr. 15, 2003, the entire contents of which are hereby incorporated by reference, and sold under the tradename PCD System by Stryker Corporation (Kalamazoo, Mich.). Still another suitable cement delivery system is disclosed in commonly owned U.S. Pat. No. 7,658,537, issued Feb. 9, 2010, the entire contents of which are hereby incorporated by reference, and sold under the tradename AutoPlex by Stryker Corporation (Kalamazoo, Mich.).

The cement delivery system 230 may include an extension tube 240 is adapted to be coupled to the coupler 104 of the delivery cannula 100, as shown in FIG. 20. The extension tube 240 includes a proximal coupler 242 coupled to the chamber 238, and a distal coupler 244 coupled to the coupler 104. The arrangement establishes communication between the chamber 238 and the sheath 160 of the delivery cannula 100. One or both of the proximal and distal couplers 242, 244 may be pivotable, and additional segments of tubing may be provided. Further construction of the extension tube 240 is disclosed in the aforementioned U.S. Provisional Patent Application No. 62/656,033. The extension tube 240 advantageously provides the physician with improved maneuverability about the patient and the surgical site without placing undue stress on the surgical instrument rigidly secured within the patient. Further, in procedures where fluoroscopy is utilized, the practitioner may deliver the curable material to within the interior region the vertebral body while avoiding unnecessary exposure to radiation.

With continued reference to FIG. 20, the spacer hub 80 is moved from the first position to the second position. The distal coupler 244 of the extension tube 240 may be coupled to the coupler 104 of the delivery cannula 100, and the cement delivery system 230 operated to direct the curable material (CM) from the chamber 238 through the delivery hub 102, through the sheath 160 including the distal portion 168 in the curve configuration, and into the cavity (CA) within the interior region of the vertebral body. It is contemplated that the sheath 160 may be proximally retracting while the curable material is being delivered so as to move the distal end 164 of the sheath 160 and locate the entry point of the curable material as desired. For example, the spacer hub 80 may be returned from the second position to the first position to facilitate the practitioner utilizing the syringe-style input previously described. The delivery cannula 100 is removed from the access cannula 44. The trocar may be reintroduced through the access cannula 44, and the access cannula 44 and trocar removed from the vertebral body. The overlying tissue may be sutured.

Figure 23:
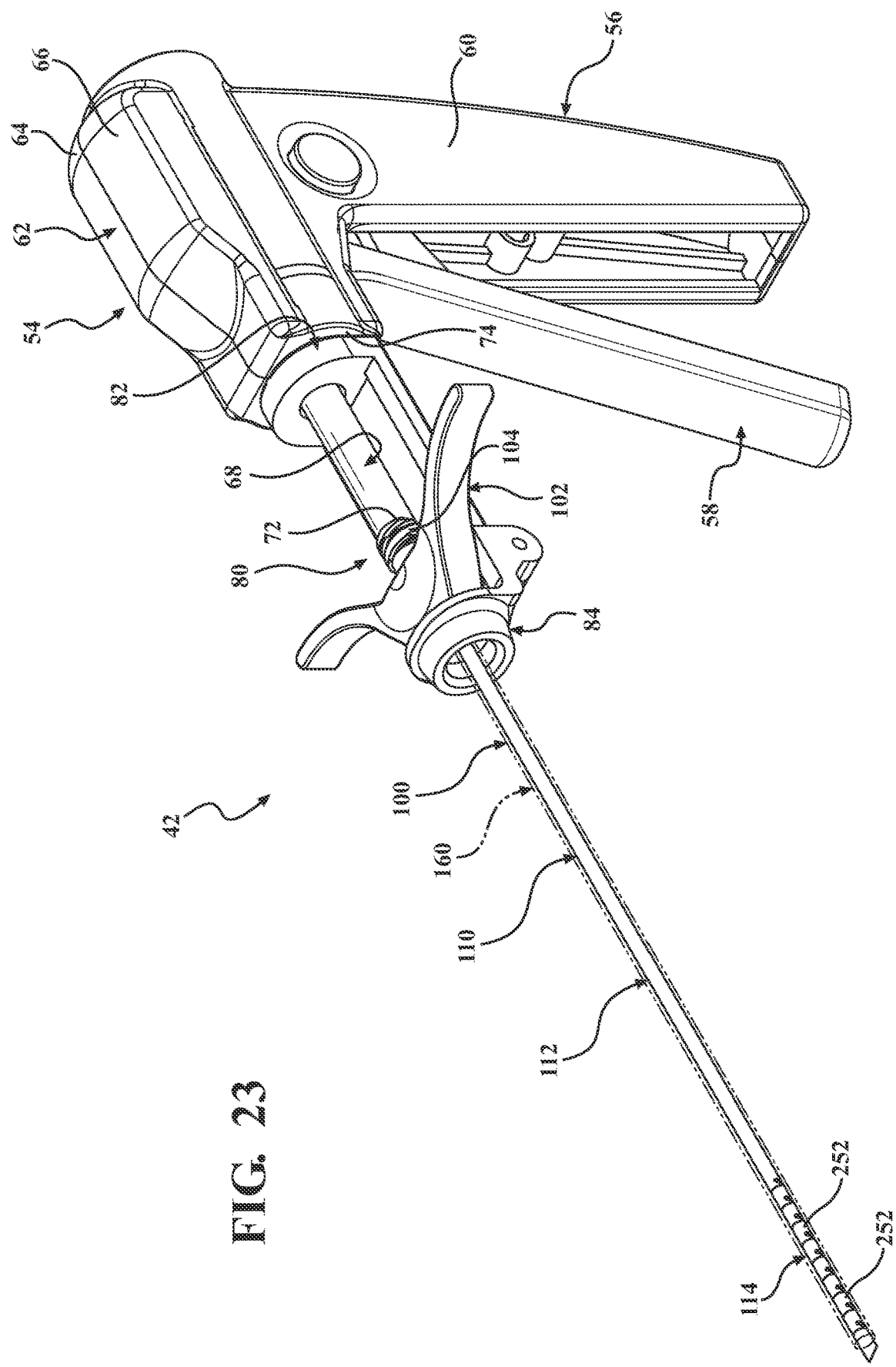
FIG. 23 is a front perspective view of the introducer device for a system for augmenting a vertebral body. The flexible sheath overlying the shaft is shown in phantom.
Figure 24:
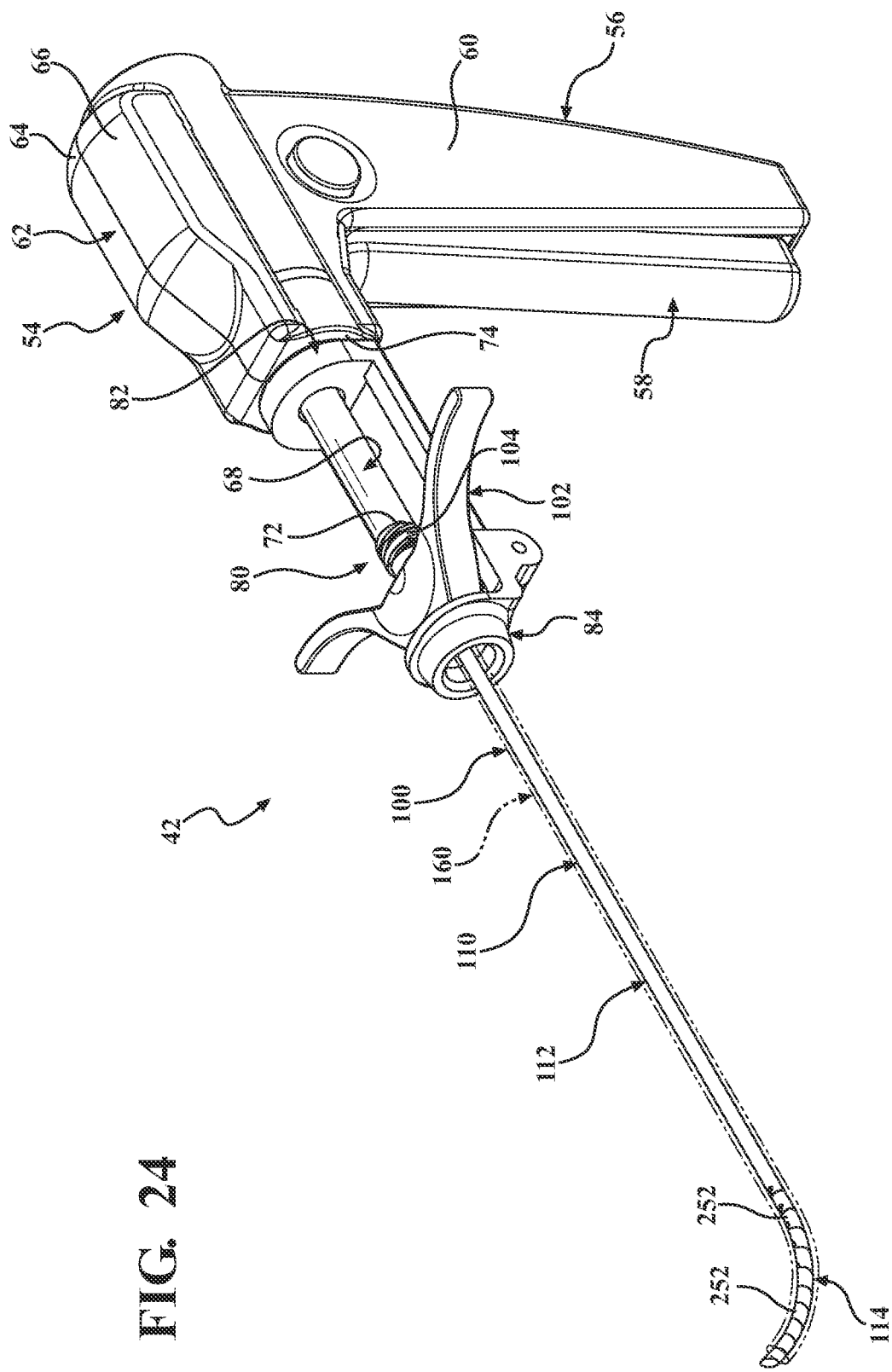
FIG. 24 is a front perspective view of the introducer device of FIG. 21 with the actuator actuated and the shaft and the flexible sheath in a curved configuration.

Referring now to FIGS. 23 and 24, another introducer device 250 is shown with the introducer device 250 configured to be directed through the access cannula 44 to locations within the interior of the vertebral body that are offset from the longitudinal axis. In at least some respects of the introducer device 250 of FIGS. 23 and 24 is similar to the introducer device 42 previously described with like numbers indicating like components. Disclosure common to the introducer devices 42, 250 is omitted in the interest of brevity and hereby incorporated by reference. FIG. 23 shows the introducer device 250 in a first or slack configuration, and FIG. 24 shows the introducer device 250 in a second or tensioned configuration. The distal portion 114 of the shaft 110 includes a plurality of links 252 interconnected to one another and configured to articulate relative to one another. The pulling element (not shown) may extend through the shaft 110 with the pulling element coupled to the actuator 54. An input to the control surface 58 of the actuator 54 facilitates the links 252 articulating relative to one another to move the introducer device 250 between the first configuration and the second configuration. The introducer device 250 and the flexible sheath 160 overlying the shaft 110 moving to the second configuration within the interior region of the vertebral body locates the distal end 120 of the shaft 110 and the distal end 164 of the sheath 160 to a location offset from the longitudinal axis. Further operation of the introducer device 250 may be described in commonly owned U.S. Pat. No. 9,839,443, issued Dec. 12, 2017, the entire contents of which are hereby incorporated by reference. The introducer device 250 is operable with the access cannula 44, the spacer hub 80, delivery cannula 100, the expandable member assembly 200, and/or the cement delivery system 230.

According to one variant, a system for augmenting a vertebral body includes an introducer device includes an actuator configured to receive an input from a user, a shaft including a rigid proximal portion coupled to the actuator and defining a proximal end of the shaft and a flexible distal portion including a pre-set curve in an unconstrained state, and a pulling element coupled to the actuator and to the shaft at or near the distal end with the pulling element extending along at least a portion of the pre-set curve, wherein tension on the pulling element is configured to be increased in response to the input provided to the actuator to move the pre-set curve from the unconstrained state to a constrained state in which the flexible distal portion at least partially straightens, and wherein the tension on the pulling element is configured to be reduced to the unconstrained state to position the distal end of the shaft within the vertebral body at a target site that is offset from the longitudinal axis; a flexible sheath at least partially overlying the shaft with the flexible sheath having a distal end positionable near the distal end of the shaft with a distal portion of the flexible sheath conforming to the flexible distal portion as the pre-set curve moves between the constrained state and the unconstrained state, wherein the introducer device is removable from the flexible sheath with the distal end of the flexible sheath remaining at the target site offset from the longitudinal axis.

According to one variant, a system for augmenting a vertebral body includes an access cannula comprising a cannula hub, and a cannula shaft extending from the cannula hub with the cannula shaft comprising a distal end positionable within the vertebral body and defining a lumen along a longitudinal axis; an introducer device including an actuator configured to receive an input from a user; a shaft comprising a rigid proximal portion coupled to the actuator and defining a proximal end of the shaft, and a flexible distal portion, wherein a length of the shaft between the proximal end and a distal end is sufficient for the shaft to extend through and be operable beyond the distal end of the access cannula, wherein the flexible distal portion comprises a pre-set curve in an unconstrained state; a pulling element coupled to the actuator and to the shaft at or near the distal end with the pulling element extending along at least a portion of the pre-set curve, wherein altering tension on the pulling element in response to the input provided to the actuator is configured to move the pre-set curve between the unconstrained state and a constrained state in which the flexible distal portion at least partially straightens; and a flexible sheath at least partially overlying the shaft with the flexible sheath comprising a distal end positionable near the distal end of the shaft such that the flexible sheath is configured to extend through and be operable beyond the distal end of the access cannula with a distal portion of the flexible sheath conforming to the flexible distal portion as the pre-set curve moves between the constrained state and the unconstrained state, wherein the introducer device is removable from the flexible sheath with the distal end of the flexible sheath remaining at the target site offset from the longitudinal axis. The system may include a biasing element operably coupled to the pulling element and the actuator with the biasing element configured to be at least initially in a stressed state to bias the pulling element to the constrained state, wherein the biasing element is further configured to relax in response to the input provided to the actuator to facilitate altering the tension on the pulling element to permit the flexible distal portion to move to the unconstrained state. The biasing element may be, for example, a compression spring. The compression spring may be in the stressed state, for example, stretched relative to its natural length. The forces from the compression spring are sufficient to overcome the forces associated with the pre-set curve biased towards the unconstrained state such that the compression spring maintains the pre-set curve in the constrained state in which the flexible distal portion at least mostly straight. Upon actuating the actuator, the compressing spring may be relaxed such that the tension on the pulling element is reduced, and the pre-set curve moves from the constrained state to the unconstrained state. As a result, the above arrangement provides an introducer device that is at least mostly straight in a default configuration and curved in an actuated configuration, which may be more intuitive and/or familiar to practitioners.

CLAUSES

Clause 1—A method of augmenting a vertebral body. The method includes positioning a distal end of an access cannula within the vertebral body such that a lumen of the access cannula provides access to an interior region of the vertebral body along a longitudinal axis. An introducer device is provided with a flexible distal portion including a pre-set curve in an unconstrained state and a distal portion of a flexible sheath conforming to the pre-set curve. An input is provided to an actuator to increase tension a pulling element to move the pre-set curve from the unconstrained state to a constrained state in which the pulling element at least partially straightens the flexible distal portion and the distal portion of the flexible sheath. The shaft of the introducer device and the flexible sheath are directed into or through the lumen of the access cannula in the constrained state. The actuator is actuated to reduce the tension on the pulling element to move the pre-set curve from the constrained state to the unconstrained state. The introducer device is advanced relative to the access cannula such that the flexible distal portion and the distal portion of the flexible sheath are positioned beyond the distal end of the access cannula to position a distal end of the flexible sheath within the vertebral body at a target site offset from the longitudinal axis.

Clause 2—The method of clause 1, wherein the step of actuating the actuator to reduce the tension on the pulling element is performed while a distal end of the introducer is at least substantially, in registration with the distal end of the access cannula.

Clause 3—The method of any one of clauses 1 and 2, further comprising removing the shaft of the introducer from the flexible sheath with the distal end of the flexible sheath remaining positioned at the target site offset from the longitudinal axis.

Clause 4—The method of clause 3, wherein the target site is a first target site, the method further comprising: providing another input to the actuator to increase the tension the pulling element while the flexible distal portion of the shaft and the distal portion of the flexible sheath are within the interior region of the vertebral body; and actuating the actuator to reduce the tension on the pulling element to move the pre-set curve from the constrained state to the unconstrained state and position the flexible distal portion of the shaft and the distal portion of the flexible sheath to facilitate repositioning the introducer device at a second target site offset from the longitudinal axis.

Clause 5—The method of clause 4, further comprising, after the step of removing the shaft of the flexible sheath and prior to the step of providing another input to the actuator to increase the tension the pulling element, directing the shaft of the introducer device through the flexible sheath to the first target site.

Clause 6—The method of clause 5, wherein directing the shaft of the introducer device through the flexible sheath to the first target site facilitates repositioning the introducer device at a second target site without requiring retraction or removal of the flexible sheath.

Clause 7—The method of any one of clauses 1-6, wherein the introducer device further includes a locking mechanism, the method further comprising actuating the locking mechanism to selectively fix the tension the pulling element, thereby fixing the pre-set curve in one of a plurality of curvatures.

Clause 8—The method of clause 7, wherein the system further includes an expandable member assembly including a balloon, the method further comprising directing the balloon through the flexible sheath to a position at or near the distal end of the sheath.

Clause 9—The method of clause 8, further comprising retracting the flexible sheath relative to the expandable member assembly to expose the balloon at the target site.

Clause 10—The method of clause 9, wherein the introducer further includes a delivery hub coupled to the flexible sheath and including a control surface, wherein the step of retracting the flexible sheath further comprises providing an input to the control surface to retract the flexible sheath while maintaining a position of the expandable member assembly.

Clause 11—The method of clause 10, wherein the expandable member assembly further includes a balloon hub and a balloon tube extending from the balloon hub with the balloon at a distal end of the balloon tube, wherein the step of providing the input to the control surface further comprises providing a syringe-style input in which a thumb maintains the position of the expandable member assembly while at least one finger actuates the control surface to draw the delivery hub towards the balloon hub.

Clause 12—The method of clause 11, wherein the system further includes a spacer hub including a distal portion engaging the cannula hub and a proximal portion spaced apart from the distal portion and engaging the balloon hub, wherein the step of providing the syringe-style input further comprises moving the control surface in the space between the distal and proximal portions of the spacer hub.

Clause 13—The method of any one of clauses 8-12, further comprising expanding the balloon to displace cancellous bone within the interior region of the vertebral body at the target site; collapsing the balloon to create a cavity; and moving the flexible sheath relative to the expandable member assembly to sheathe the balloon.

Clause 14—The method of clause 13, further comprising removing the expandable member assembly from the flexible sheath.

Clause 15—The method of clause 14, wherein the system includes a curable material delivery device, wherein the distal and proximal portions of the spacer hub are pivotably coupled to one another, the method further comprising: pivoting the proximal portion relative to the distal portion so that the proximal portion is no longer aligned with the distal portion; coupling the curable material delivery device to the delivery hub; and directing curable material from the curable material delivery device through the delivery hub and the flexible sheath to within the cavity within the interior region of the vertebral body.

Clause 16—The method of any one of clauses 1-15, wherein the access cannula includes a cannula shaft, a shaft hub rigidly coupled to the cannula shaft and providing a datum, and a tuning hub movably coupled to the shaft hub and including an interference surface, the method further comprising moving the tuning hub relative to the shaft hub to selectively adjust an axial position of the interference surface relative to relative to the datum.

Clause 17—The method of clause 16, wherein each of the shaft hub and the tuning hub comprises complementary threading, wherein the step of moving the tuning hub relative to the shaft hub further comprises twisting the tuning hub relative to the shaft hub.

Clause 18—A method for augmenting a vertebral body. A distal end the access cannula is positioned within the vertebral body such that a lumen of the access cannula provides access to an interior region of the vertebral body along a longitudinal axis. A shaft of the introducer device and the flexible sheath are directed through the lumen of the access cannula in a straightened configuration. The flexible distal portion and a distal portion of the flexible sheath extends beyond the distal end of the access cannula. The flexible distal portion and the distal portion of the flexible sheath are configured to move from the straightened configuration to a first curved configuration within the vertebral body. A first lateral x-ray image from the x-ray device is viewed on a display in which the at least two markers are spaced apart from one another at a first lateral distance in the first curved configuration. The introducer device is operated to move the flexible distal portion and the distal portion of the flexible sheath from the first curved configuration to a second curved configuration. A second lateral x-ray image from the x-ray device is viewed on the display in which the at least two markers are spaced apart from one another at a second lateral distance different than the first distance.

Clause 19—The method of clause 18, further comprising: viewing on the display a first anterior-posterior (AP) x-ray image from the x-ray device in which the at least two markers are spaced apart from one another at a first AP distance in the first curved configuration; and viewing on the display a second AP x-ray image from the x-ray device in which the at least two markers are spaced apart from one another at a second AP distance different than the first distance.

Clause 20—The method of any one of clauses 18 and 19, wherein the second curved configuration has a greater curvature than the first curved configuration when the second lateral distance is less than the first lateral distance.

Clause 21—The method of any one of clauses 18-21, wherein the second curved configuration has a greater curvature than the first curved configuration when the second AP distance is greater than the first AP distance.

The foregoing disclosure is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A system for treating a vertebral body, the system comprising:
   an access cannula comprising a cannula hub, and a cannula shaft extending from the cannula hub and comprising a distal end positionable within the vertebral body;
   a delivery cannula comprising a delivery hub, a sheath extending from the delivery hub and configured to be operable beyond the distal end of the access cannula, wherein the delivery hub is movable relative to the cannula hub such that the sheath is slidably disposed within the cannula shaft;
   an instrument comprising an instrument hub, and an elongate member extending from the instrument hub and configured to be removably directed within the sheath; and a spacer hub comprising a distal portion configured to removably engage the cannula hub, and a proximal portion configured to be engaged by the instrument hub to facilitate the delivery hub receiving a syringe-style input from a user in which a proximal control surface engaged by a thumb of a user opposes forces from a proximally-directed input force to the delivery hub so as to move the delivery cannula proximally relative to the access cannula and expose a distal end of the elongate member within the vertebral body, and wherein the spacer hub comprises a stop surface configured to provide a terminus of proximal movement of the delivery hub within a void space of the spacer hub.

2. The system of claim 1, wherein the distal portion and the proximal portion are spaced apart from one another to define the void space, and wherein the delivery hub is configured to be movably disposed within the void space.

3. The system of claim 1, wherein the spacer hub further comprises two sides defining opposed slots, and wherein the delivery hub comprises wings extending through the opposed slots and configured to receive fingers of the user to facilitate the syringe-style input.

4. The system of claim 1, wherein the proximal control surface is planar.

5. The system of claim 1, wherein the proximal control surface comprises gripping features.

6. The system of claim 1, wherein the instrument hub is a balloon hub and defines a borehole positioned distal to the proximal control surface such that an entirety of the proximal control surface is unobstructed to receive the thumb of the user, and wherein the borehole is configured to be arranged in fluid communication with a fluid source.

7. The system of claim 6, wherein the instrument is an expandable member assembly in which the elongate member is a balloon tube extending from the balloon hub, and wherein the expandable member assembly comprises a balloon at a distal end of the balloon tube.

8. The system of claim 1, wherein the instrument is an electrode assembly that is flexible and configured to be directed through the sheath with the distal portion of the sheath remaining curved.

9. The system of claim 1, further comprising an implant, wherein the instrument is configured to deploy the implant with the distal portion of the sheath remaining curved.

10. The system of claim 1, further comprising a steering instrument removably disposed within the sheath, wherein the steering instrument comprises:
an actuator;
a shaft coupled to the actuator and comprising a flexible distal portion having a pre-set curve in an unconstrained state; and
a pulling element coupled to the actuator and the shaft and configured to be tensioned to move the pre-set curve from the unconstrained state to a constrained state in which the flexible distal portion at least partially straightens.

11. The system of claim 1, wherein the distal portion of the sheath further comprises at least two radiopaque indicia that are spaced apart from one another such that, as the distal portion is curved within the vertebral body, relative positions between the at least two radiopaque indicia is viewable on radiography to determine an extent of a curve of the sheath.

12. A system for treating a vertebral body, the system comprising:

an access cannula comprising a cannula hub, and a cannula shaft extending from the cannula hub and comprising a distal end positionable within the vertebral body;
a delivery cannula comprising a delivery hub, a sheath extending from the delivery hub and configured to be operable beyond the distal end of the access cannula, wherein the delivery hub is movable relative to the cannula hub such that the sheath is slidably disposed within the cannula shaft;
an instrument comprising an instrument hub, and an elongate member extending from the instrument hub and configured to be removably directed within the sheath; and
a spacer hub comprising a proximal portion configured to be engaged by the instrument hub, wherein the spacer hub defines a slot, wherein the delivery hub comprises a wing extending through the slot, wherein the wing is configured to receive a proximally-directed input force from a user to move the delivery cannula proximally relative to the access cannula to expose a distal end of the elongate member within the vertebral body.

13. The system of claim 12, wherein the instrument hub comprises a flanged portion having a proximal control surface sized to receive a thumb of the user.

14. The system of claim 13, wherein the proximal control surface is planar.

15. A system for treating a vertebral body, the system comprising:
an access cannula comprising a cannula hub, and a cannula shaft extending from the cannula hub and comprising a distal end positionable within the vertebral body;
a delivery cannula comprising a delivery hub, a sheath extending from the delivery hub and configured to be operable beyond the distal end of the access cannula, wherein the delivery hub is movable relative to the cannula hub such that the sheath is slidably disposed within the cannula shaft;
an expandable member assembly comprising a balloon hub adapted to be coupled to a fluid source, a balloon tube extending from the balloon hub and sized to be slidably inserted within the sheath, and a balloon coupled to a distal end of the balloon tube and configured to be inflated with fluid from the fluid source to displace cancellous bone within the vertebral body; and
a spacer hub comprising a distal portion configured to engage the cannula hub, and a proximal portion configured to be engaged by the balloon hub, wherein the balloon hub comprises a flanged portion defining a proximal control surface arranged to be engaged by a thumb of a user to oppose forces from the delivery hub receiving a proximally-directed input from a user to expose the balloon within the vertebral body.

16. The system of claim 15, wherein the spacer hub further comprises two sides defining opposed slots, and wherein the delivery hub comprises wings extending through the opposed slots and configured to receive fingers of the user to facilitate the proximally-directed input.

17. The system of claim 16, wherein the proximal control surface is planar.

18. The system of claim 16, wherein a distance by which the wings are movable proximally within the opposing slots is greater than a length of the balloon.

19. The system of claim 15, wherein the balloon hub defines a borehole positioned distal to the flanged portion such that an entirety of the proximal control surface is unobstructed to receive the thumb of the user, wherein the borehole is configured to be arranged in fluid communication with the fluid source.

\* \* \* \* \*